(12) United States Patent
Karg et al.

(10) Patent No.: US 6,620,383 B1
(45) Date of Patent: Sep. 16, 2003

(54) MICROVOLUME LIQUID DISPENSING DEVICE

(75) Inventors: Jeffrey A. Karg, Hopkinton, MA (US); Douglas W. Kroncke, Boston, MA (US)

(73) Assignee: Boston Innovation Inc., MA (US)

( * ) Notice: Subject to any disclaimer, the term of this patent is extended or adjusted under 35 U.S.C. 154(b) by 128 days.

(21) Appl. No.: 09/591,803

(22) Filed: Jun. 12, 2000

Related U.S. Application Data

(60) Provisional application No. 60/185,810, filed on Feb. 29, 2000.

(51) Int. Cl.[7] ................................................ B01L 3/02
(52) U.S. Cl. .................... 422/100; 436/180; 73/864.13; 73/864.16; 73/864.22; 73/864.24; 73/864.34; 73/864.64; 222/133; 222/71
(58) Field of Search .......................... 422/100; 436/180; 222/133, 71; 73/864.13, 864.16, 864.22, 864.24, 864.34, 864.64

(56) References Cited

U.S. PATENT DOCUMENTS

| | | | |
|---|---|---|---|
| 3,167,398 A | 1/1965 | Whittington | |
| 4,180,239 A | 12/1979 | Valukis | |
| 4,268,481 A | * 5/1981 | Suovaniemi et al. | ........ 222/391 |
| 4,487,081 A | 12/1984 | De Vaughn et al. | |
| 4,806,313 A | 2/1989 | Ebersole et al. | |
| 4,844,868 A | 7/1989 | Rokugawa | |
| 4,875,605 A | 10/1989 | Weston | |
| 4,973,450 A | 11/1990 | Schlüter | |
| 5,074,154 A | * 12/1991 | Allen et al. | .................. 417/553 |
| 5,226,462 A | 7/1993 | Carl | |
| 5,272,926 A | 12/1993 | Wilkins | |
| 5,421,492 A | 6/1995 | Barger et al. | |
| 5,440,940 A | 8/1995 | Wilkins | |
| 5,454,268 A | * 10/1995 | Kim | .................. 422/100 |
| 5,741,554 A | 4/1998 | Tisone | |
| 5,743,960 A | 4/1998 | Tisone et al. | |
| 5,756,050 A | 5/1998 | Ershow et al. | |
| 5,770,158 A | 6/1998 | Eischen et al. | |
| 5,876,675 A | 3/1999 | Kennedy | |
| 5,962,329 A | 10/1999 | Ershov et al. | |
| 5,976,470 A | * 11/1999 | Maiefski et al. | ............. 222/485 |
| 6,024,925 A | 2/2000 | Little et al. | |
| 6,063,339 A | 5/2000 | Tisone et al. | |
| 6,109,717 A | 8/2000 | Kane et al. | |
| 6,182,719 B1 | 2/2001 | Yahiro | |
| 6,416,718 B1 | * 7/2002 | Maiefski et al. | ......... 222/144.5 |

FOREIGN PATENT DOCUMENTS

| | | | |
|---|---|---|---|
| WO | WO 90/08075 | * | 7/1990 |
| WO | WO 98/04358 | * | 2/1998 |
| WO | WO 99/10099 | | 3/1999 |
| WO | WO 99/15876 | | 4/1999 |
| WO | WO 99/17749 | | 4/1999 |
| WO | WO 99/42752 | | 8/1999 |
| WO | WO 99/43432 | | 9/1999 |
| WO | WO 99/61881 | | 12/1999 |
| WO | WO 00/24511 | | 5/2000 |

* cited by examiner

*Primary Examiner*—Jill Warden
*Assistant Examiner*—Elizabeth Quan
(74) *Attorney, Agent, or Firm*—Fish & Richardson P.C.

(57) ABSTRACT

Devices and methods for integrated packaging, shipping, storage and precise dispensing of extremely small volumes of liquids such as aqueous solutions and compounds dissolved in organic solvents are disclosed. Devices of the invention include a sealed reservoir with an integrated metering tap. The tap includes a metering tube, which is translatable between a fill position inside the reservoir and an expel position outside the reservoir. The metering tube includes: (1) a tube end closure in a lower portion of the tube, (2) a port above the tube end closure, and (3) a piston in an upper portion of the tube. The piston is movable between a down position that seals the side port and an up position above the port. Movement of the piston from the up position to the down position can displace from 10 nanoliters to 20 microliters, e.g., from 20 nanoliters to 2 microliters, or 50 nanoliters to 500 nanoliters. Integrated arrays of reservoir/tap units are suitable for use in automated, multiwell formats such as those commonly used for high-throughput screening.

16 Claims, 27 Drawing Sheets

MICROVOLUME LIQUID DISPENSING DEVICE

This application claims priority from U.S. provisional application Ser. No. 60/185,810, filed Feb. 29, 2000.

TECHNICAL FIELD

This invention relates to liquid handling and microfluidics.

BACKGROUND

The development of automated combinatorial chemistry systems and ultra-high throughput screening systems have dramatically increased the number of compounds per unit time being synthesized and screened in drug discovery programs. Such technology involves rapid handling of large numbers of very small samples. For example, thousands of new compounds per week may be produced, with each compound being concentrated in a total volume of only 50 microliters. Microliter amounts of sample often must suffice for hundreds of screening assays. Conventionally, aliquots of the concentrated, liquid sample are dispensed using "sip and spit" liquid handling technology, diluted in an appropriate medium, and re-dispensed into an assay mixture, again using sip and spit technology. This "reformatting" process adds complexity to the overall process, thereby increasing time and cost per assay. In addition, reformatting generates waste of valuable sample material.

SUMMARY

The invention features a method of packaging a liquid for storage and metered dispensing of nanoliter or microliter volumes. The method includes: (a) providing a reservoir; (b) dispensing the liquid into the reservoir; and (c) incorporating a dispensing tap to form a reservoir/tap unit sealed against entry of air and leakage of the liquid. The dispensing tap includes a translatable metering tube that contains a tube end closure, a port, and a translatable piston. The reservoir can be sealed against entry of light. In some embodiments of the invention, the liquid is a solution of one or more chemical compounds. In some embodiments, liquid-contacting surfaces of the reservoir and tap are resistant to damage by acids, bases, salts and organic solvents. In some embodiments, the method further includes inserting a fill pin before dispensing the liquid into the reservoir. The fill pin can be inserted from below the reservoir and then removed by inserting the translatable metering tube from above the reservoir to replace the fill pin.

The invention also features a method of dispensing a metered, nanoliter or microliter amount of a liquid into a liquid-receiving unit. The method includes: (a) providing a sealed reservoir with an integrated dispensing tap that includes a translatable metering tube; (b) aligning the tap over the liquid-receiving unit; (c) actuating the tap so that it dispenses a metered, nanoliter or microliter amount of the liquid into the liquid-receiving unit. The translatable metering tube includes a tube end closure, a port, and a translatable piston. The metered amount of liquid can be from 10 nanoliters to 20 microliters, e.g., from 100 nanoliters to 2 microliters, or 50 nanoliters to 500 nanoliters. Preferably, the tap does not contact the liquid-receiving unit surface, and the dispensed liquid breaks contact with the tap before contacting the liquid-receiving unit surface. Preferably, the tap contains minimal, e.g., substantially zero, dead volume. In some embodiments, actuating the tap includes: translating the tube so that the port is inside the reservoir; drawing liquid from the reservoir through the port and into the tube; translating the tube so that the port is outside the reservoir; and expelling liquid from the tube, through the port. The liquid can be drawn into the tube by translating the piston upward. The liquid then can be expelled from the tube by translating the piston downward. The method can include propelling the expelled liquid away from the port and toward the liquid-receiving unit surface. Such propelling can be accomplished by applying a suitable propelling fluid to the expelled liquid. The propelling fluid can be a propelling liquid, e.g., an aqueous liquid or an organic solvent; or a propelling gas, e.g., air, nitrogen or argon. The dispensed liquid can be, e.g., a solution of one or more chemical compounds. The liquid-contacting surfaces of the reservoir and tap can be made of a material resistant to damage by acids, bases and organic solvents.

The invention also features devices for storing and dispensing metered, nanoliter or microliter amounts of liquid into a liquid-receiving unit.

An offset nozzle-type device includes: a sealed reservoir with an integrated metering tap. The tap includes a metering tube and a fluid output channel. The metering tube is translatable between a fill position inside the reservoir and an expel position outside the reservoir. The metering tube includes: (2) a tube end closure in a lower portion of the tube, (2) a port above the tube end closure, and (3) a piston in an upper portion of the tube. The piston is movable between a down position that seals the side port and an up position above the port. The fluid output channel has an upper portion in fluid communication with the port when the tube is in the expel position and a lower portion terminating in a nozzle tip. Movement of the piston from the up position to the down position can displace from 10 nanoliters to 20 microliters, e.g., from 20 nanoliters to 2 microliters, or 50 nanoliters to 500 nanoliters. The device can include a compressed gas inlet port in fluid communication with the fluid output channel at a point upstream of the port when the tube is in the expel position.

An in-line nozzle-type device includes a sealed reservoir with an integrated metering tap. The metering tap includes a metering tube and a nozzle. The metering tube is translatable between a fill position inside the reservoir and an expel position outside the reservoir. The metering tube includes: (2) a tube end closure in a lower portion of the tube, (2) a port above the tube end closure, and (3) a piston in an upper portion of the tube. The piston is movable between a down position that seals the port and an up position above the port. The nozzle includes a fluid output channel through which the tube extends when in the down position. The fluid output channel has an upper end in fluid communication with a compressed gas path, and a lower end terminating in a nozzle tip. Movement of the piston from the up position to the down position can displaces from 10 nanoliters to 20 microliters, e.g., from 20 nanoliters to 2 microliters, or 50 nanoliters to 500 nanoliters.

A nozzleless-type device includes a sealed reservoir with an integrated metering tap. The metering tap includes a metering tube. The metering tube is translatable between a fill position inside the reservoir and an expel position outside the reservoir. The metering tube includes: (2) a tube end closure in a lower portion of the tube, (2) a port above the tube end closure, a (3) a piston in an upper portion of the tube, and (4) a lower end. The piston is movable between a down position that seals the port and an up position above the port. A compressed gas path, which includes one or more compressed gas outlets located above the port, is located to deliver a downward gas stream across the port, when the metering tube is in the expel position. Movement of the piston from the up position to the down position can displace from 10 nanoliters to 20 microliters, e.g., from 20 nanoliters to 2 microliters, or 50 nanoliters to 500 nanoliters. In some embodiments, the lower end of the metering tube is tapered to a point.

As used herein, "liquid-receiving unit" (LRU) means: (a) a defined or addressable area on a flat liquid-receiving surface, e.g., a glass slide; or (b) a depression or well in a liquid-receiving container, e.g., a microtiter plate, or (c) a receptacle, e.g., a test tube, vial, or bottle.

As used herein, "reservoir/tap unit" means a single tapped reservoir.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 depicts an offset nozzle embodiment.

FIG. 14 depicts an in-line nozzle embodiment.

FIG. 19 shows a bolus of expelled liquid emerging from a port in the side of the tube.

Throughout the various drawings, like reference numbers indicate like elements.

DETAILED DESCRIPTION

The invention provides methods and devices for integrated packaging, shipping, storage, and precision dispensing of extremely small volumes of liquids, e.g., aqueous solutions and compounds dissolved in organic solvents. In some embodiments, devices and methods of the invention are employed in the form of a single reservoir/tap unit operated in a manual or automated system. In other embodiments, devices and methods of the invention are incorporated into an array. The array can be an automated, multi-well format, e.g., a system used in high throughput screening (HTS) or ultra-high throughput screening (UHTS). By virtue of a metering tap integrated with each reservoir in an array of reservoir/tap units, the invention advantageously avoids the use of conventional sip and spit technology. Consequently, multi-well plate assays can be performed without reformatting, i.e., transferring aliquots of concentrated samples from storage plates to working plates, diluting on working plates, transferring diluted samples from working plates to assay plates, etc. This maximizes speed and efficiency. Entire sets of samples, e.g., compounds for screening, can be stored and/or shipped conveniently in a single cassette, which can be plugged into an HTS or UHTS system, where nanoliter volumes of concentrated sample can be dispensed directly onto assay plates without reformatting. Because the reservoir/tap units in an array are isolated from each other, single-channel dispensing is achieved, and each reservoir/tap unit is individually addressable. Because each reservoir/tap unit in an array (cassette) can be sealed against air, moisture and light, labile compounds can be stored and handled under favorable conditions.

Figure 1:
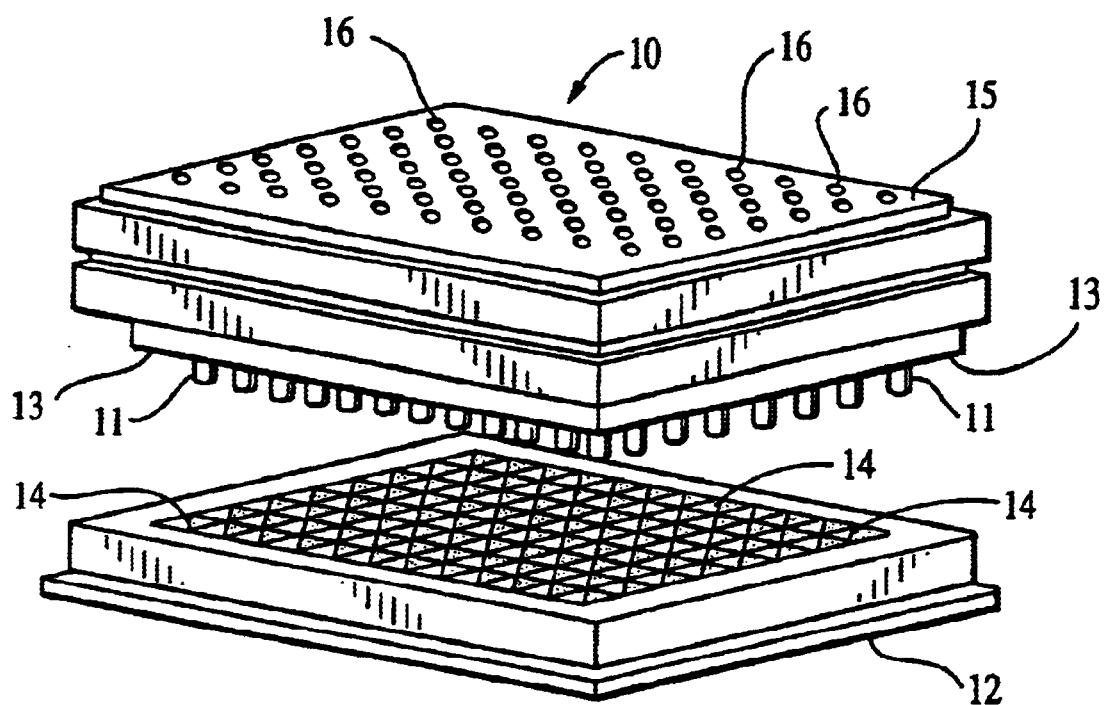
FIG. 1 is a perspective view of a device for integrated storage and single-channel dispensing of small volumes of liquids. The depicted device contains a 96-unit array of integrated reservoir/tap units. The 96 units are arranged so that each of the 96 tips aligns with one well of a conventional 96-well microtiter plate.

FIG. 1 is a perspective view of a device 10 according to the invention for storing and dispensing liquid into a conventional 96-well microtiter plate 12. Protruding from lower surface 13 of device 10 are 96 flow tips 11 arranged so that when device 10 is aligned above 96-well microtiter plate 12, each tip 11 is above a different one of the 96 wells 14 in plate 12. On the upper surface 15 of device 10 are 96 mechanical interfaces 16 for tap actuation. Operation of each interface 16 actuates a tap whose flow path tip 11 is located beneath that interface 16.

Figure 2:
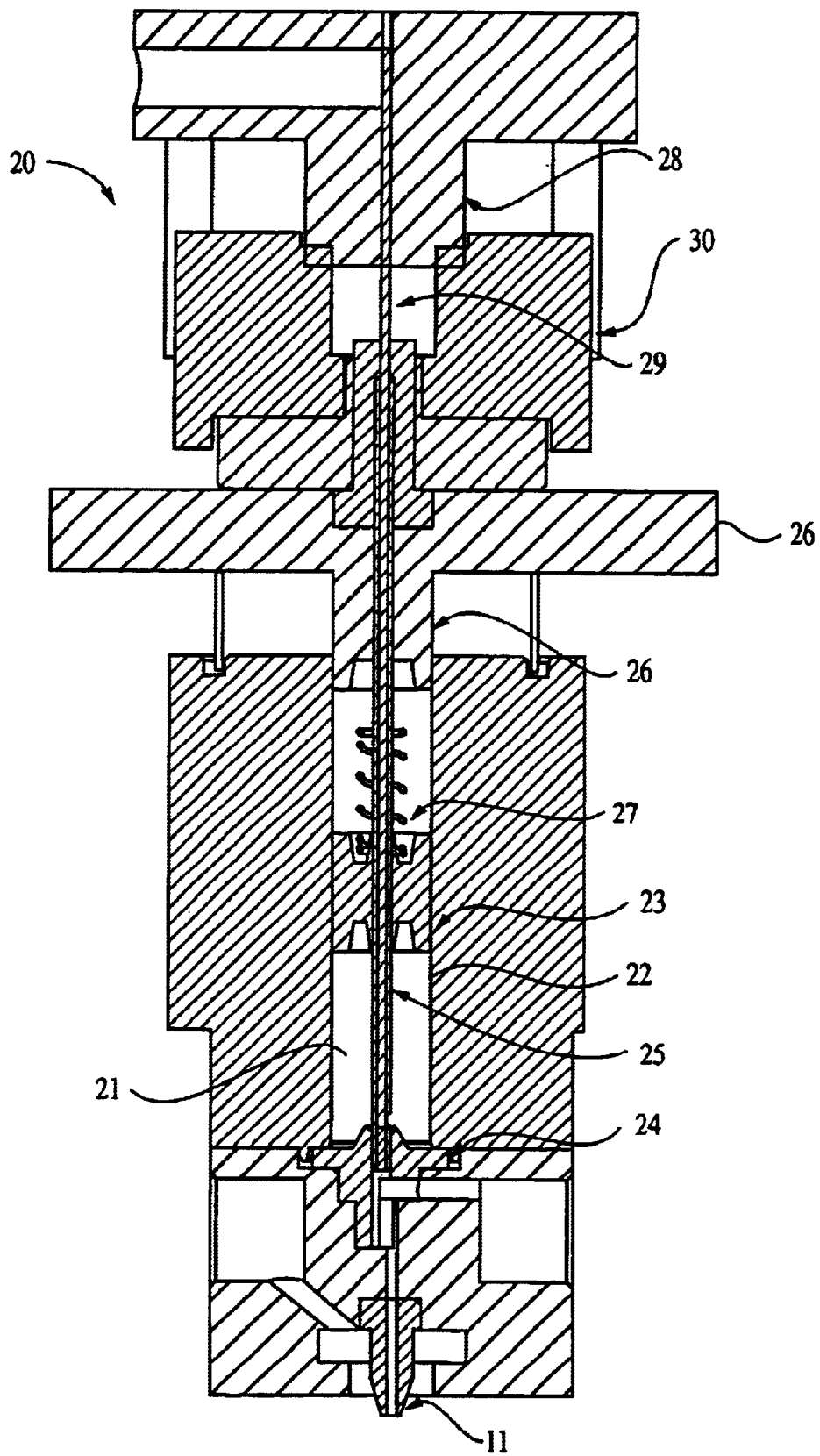
FIG. 2 is a sectional view of a single reservoir/tap unit. The unit has a metering tube which is in the up position.

FIG. 2 is a sectional view of a single reservoir/tap unit 20. The unit 20 contains a reservoir 21 formed by a cylinder wall 22, sliding seal 23 and lower seal 24. The unit 20 also contains a metering tube 25, tube handle 26, tube handle spring 27, piston handle 28, piston 29, and piston handle stop 30. The embodiment depicted in FIG. 2 is an example of an offset nozzle embodiment, because nozzle tip 11 is not directly in line with metering tube 25. FIG. 2 shows the tube 25 and tube handle 26 in the up position. Tube handle 26 and piston handle 28 are included in each mechanical interface 16 shown in FIG. 1.

Figure 3:
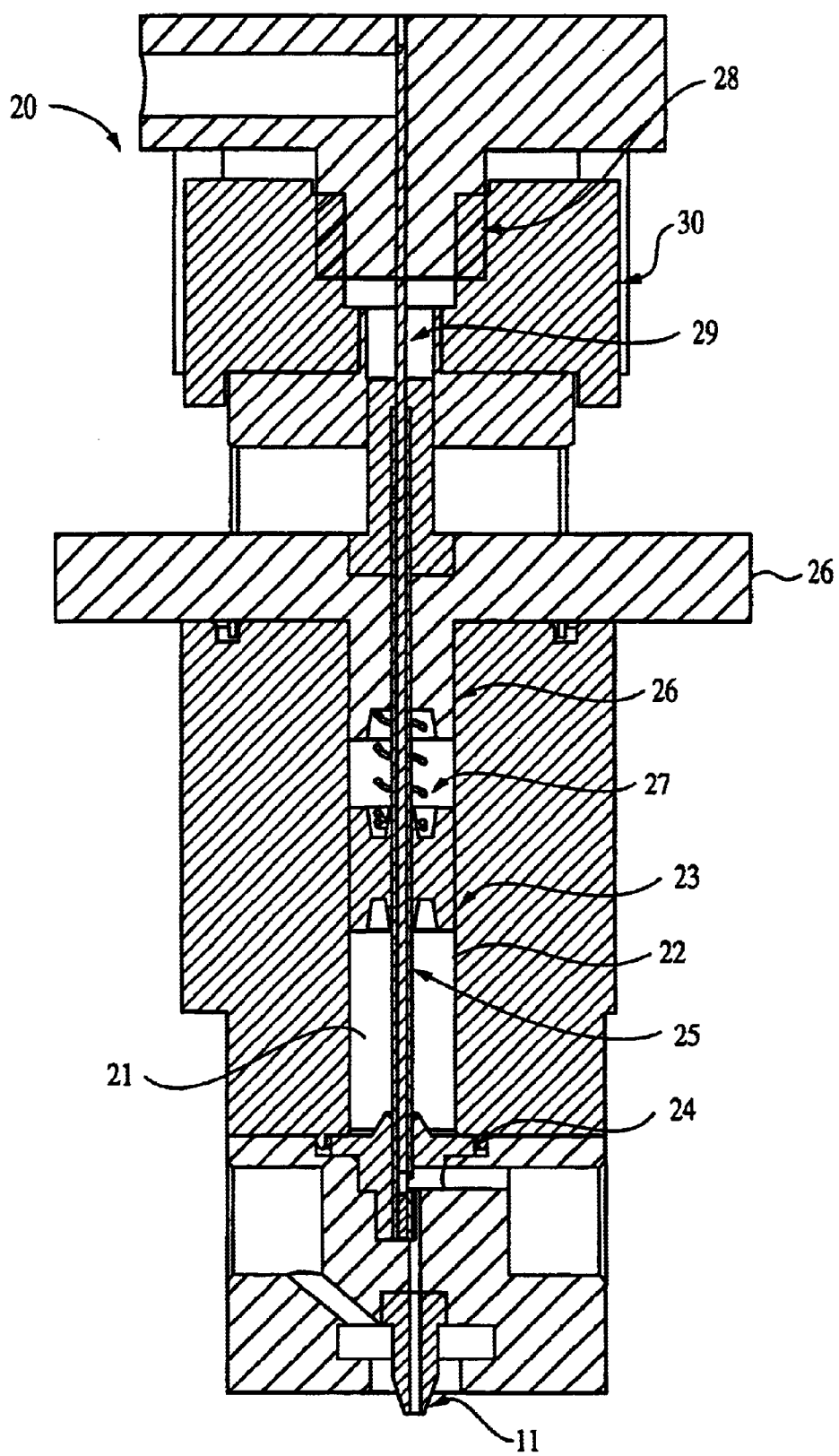
FIG. 3 is a sectional view of the reservoir/tap unit shown in FIG. 2, but with the metering tube in the down position.

Reservoir 21 contains minimal air space. Therefore, liquid in reservoir 21 is essentially coextensive with the volume of reservoir 21. As liquid is metered from reservoir 21, sliding seal 23 slides downward reducing the volume of reservoir 21 so that remnant liquid in reservoir 21 remains coextensive with the volume of reservoir 21. FIG. 3 is a sectional view of a single unit 20 in which the tube 25 is in the down position.

Figure 4:
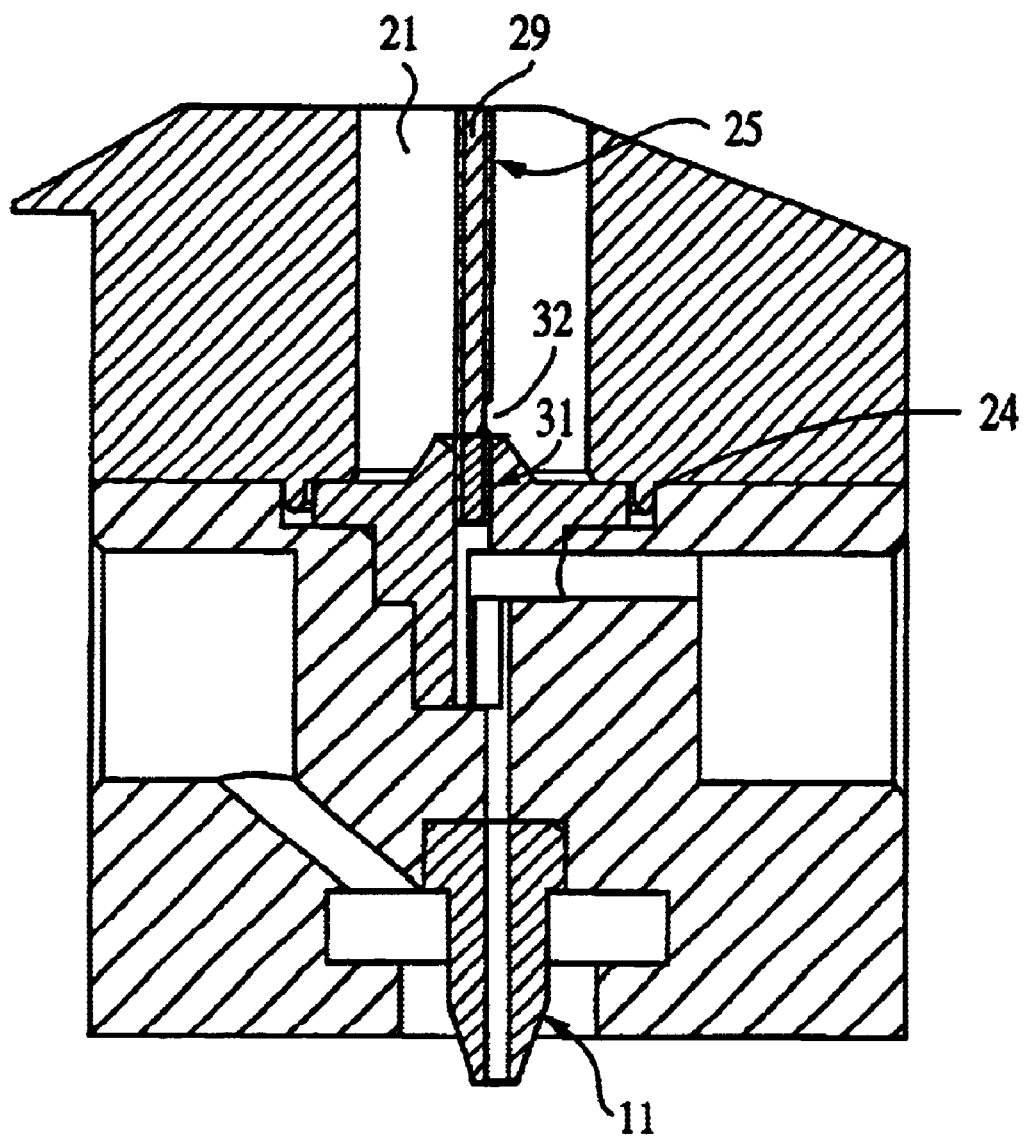
FIG. 4 is a detail from FIG. 2. The enlarged detail view shows the tube in the up position, and a piston in the tube. The piston is in the down position, where it rests against a tube plug.
Figure 5:
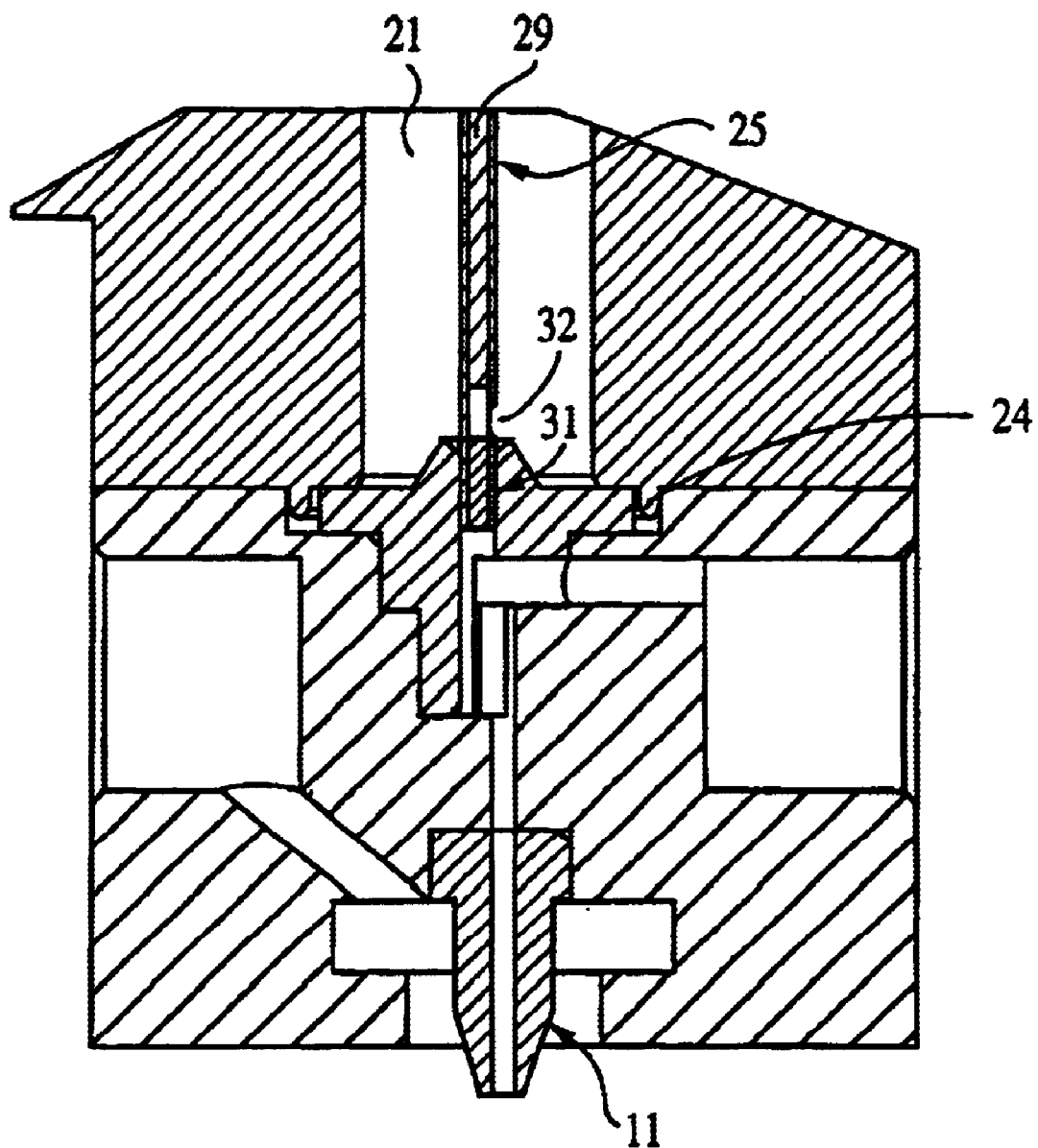
FIG. 5 is the same as FIG. 4, except that the piston is raised into an up position.

FIG. 4 is a detail from FIG. 2, in which tube 25 is in the up position and piston 29 is in the down position. In the down position, piston 29 rests against tube plug (tube end closure) 31 so that piston 29 closes and seals tube port 32, thereby blocking entry of liquid from reservoir 21 into tube 25. FIG. 5 is the same as FIG. 4, except that piston 29 is raised into an up position. Raising piston 29 opens tube port 32 and draws a metered amount of liquid from reservoir 21 into tube 25, with the metered amount depending on the height to which piston 29 is raised.

Figure 8:
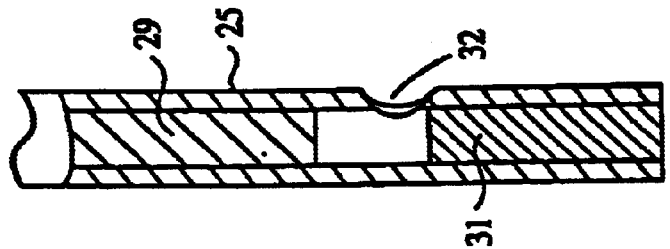
FIG. 8 is an enlarged sectional view (rotated 90° relative to FIG. 6) showing a lower portion of the tube, the tube plug, and a lower portion of the piston.
Figure 7:
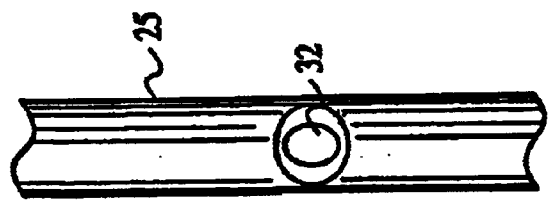
FIG. 7 is a detail enlarged from FIG. 6, showing the tube port.
Figure 6:
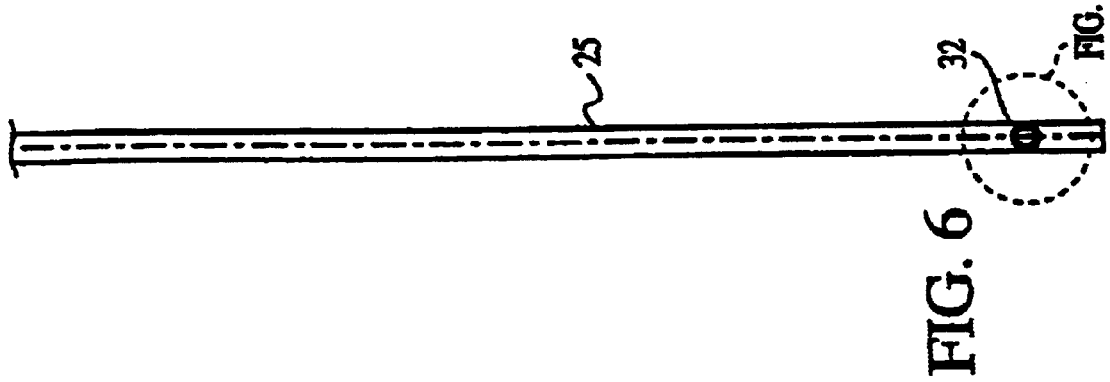
FIG. 6 is an enlarged, front view of a metering tube. A tube port, through which liquid enters and leaves the tube is visible near the lower end of the tube.

FIG. 6 is an enlarged, front view of metering tube 25, showing tube port 32. FIG. 7 is a detail from FIG. 6, showing tube port 32. FIG. 8 is an enlarged sectional view (rotated 90° relative to FIG. 6) showing a lower portion of tube 25, tube plug 31, and a lower portion of piston 29.

Figure 9:
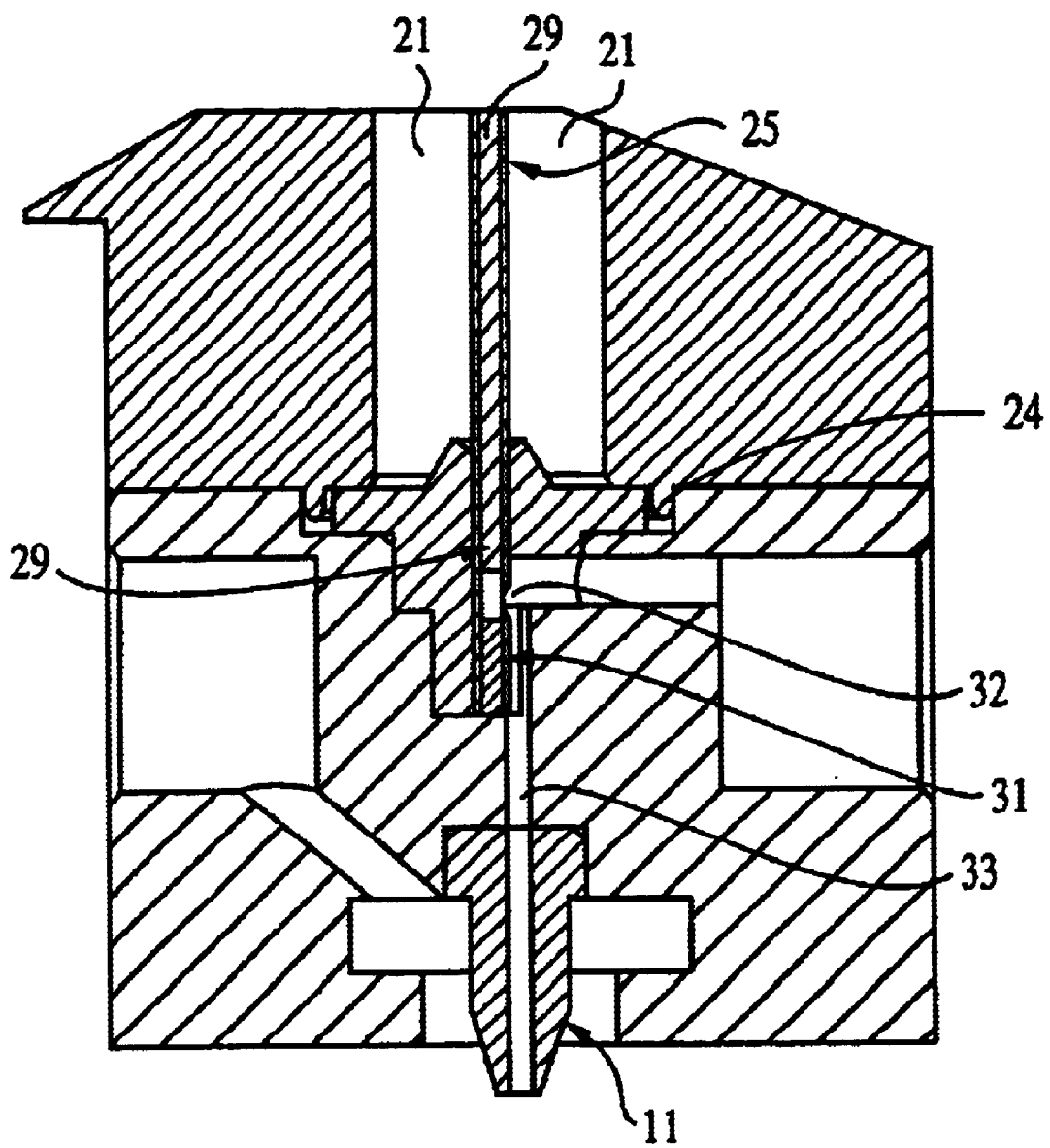
FIG. 9 is a sectional view (detail) of a reservoir/tap unit in which the metering tube is in the down position, and the piston is in an up position.

In illustrating operation of device 20, FIG. 9 is sequential, following FIG. 5. In FIG. 9, metering tube 25 has been translated downward into the down position, with piston 29 remaining in the up position, i.e., same position relative to tube 25. In FIG. 9, downward translation of tube 25 through lower seal 24 has taken port 32 out of reservoir 21 and placed port 32 in fluid communication with fluid output channel 33. The next sequential step is lowering of piston 29 into the down position, in which piston 29 rests against tube plug 31. This lowering of piston 29 expels liquid (not shown) from tube 25 and into fluid output path 33.

Figure 10:
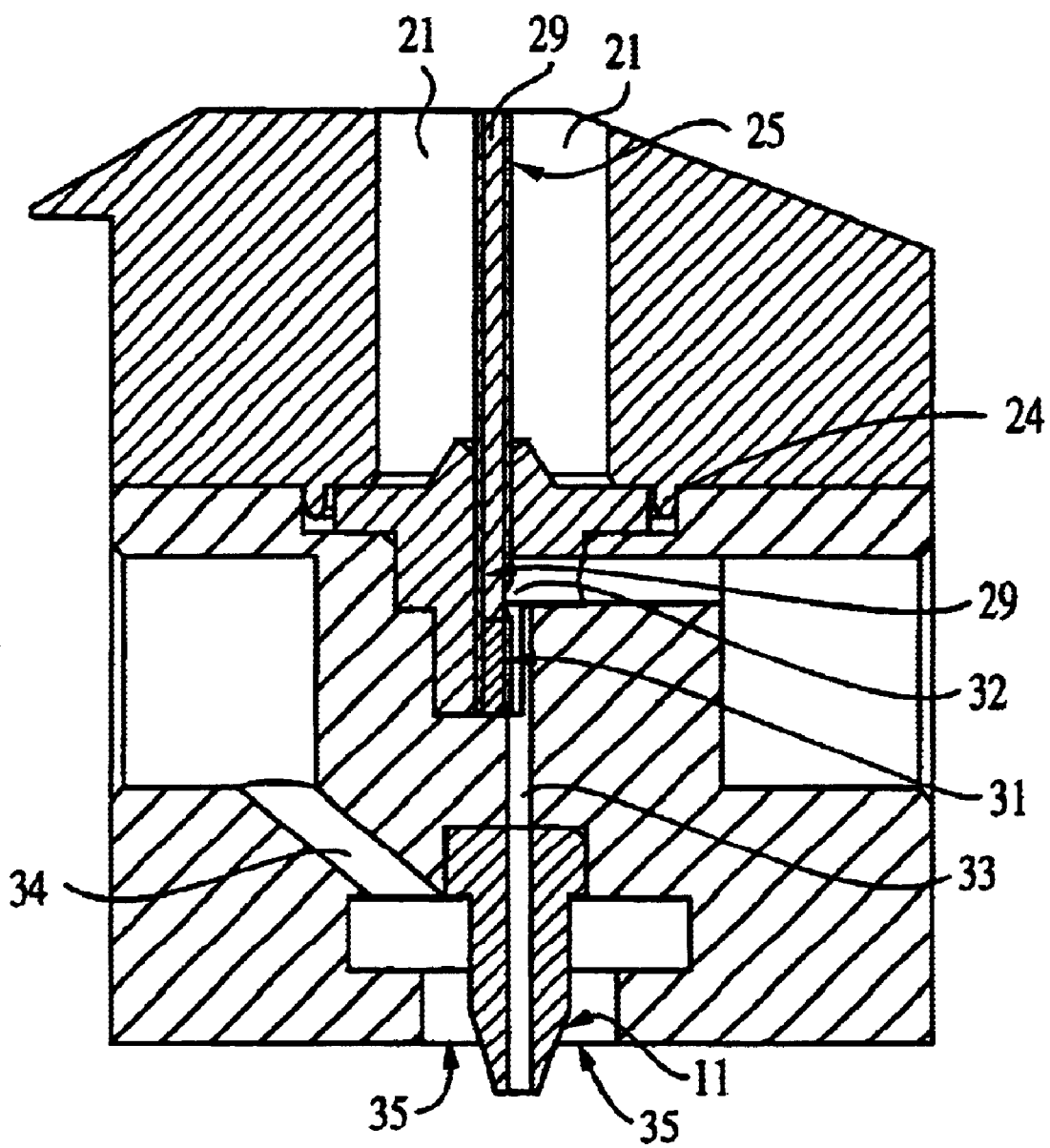
FIG. 10 is a sectional view (detail) of a reservoir/tap unit in which the metering tube is in the down position, and the piston is in a down position.
Figure 11:
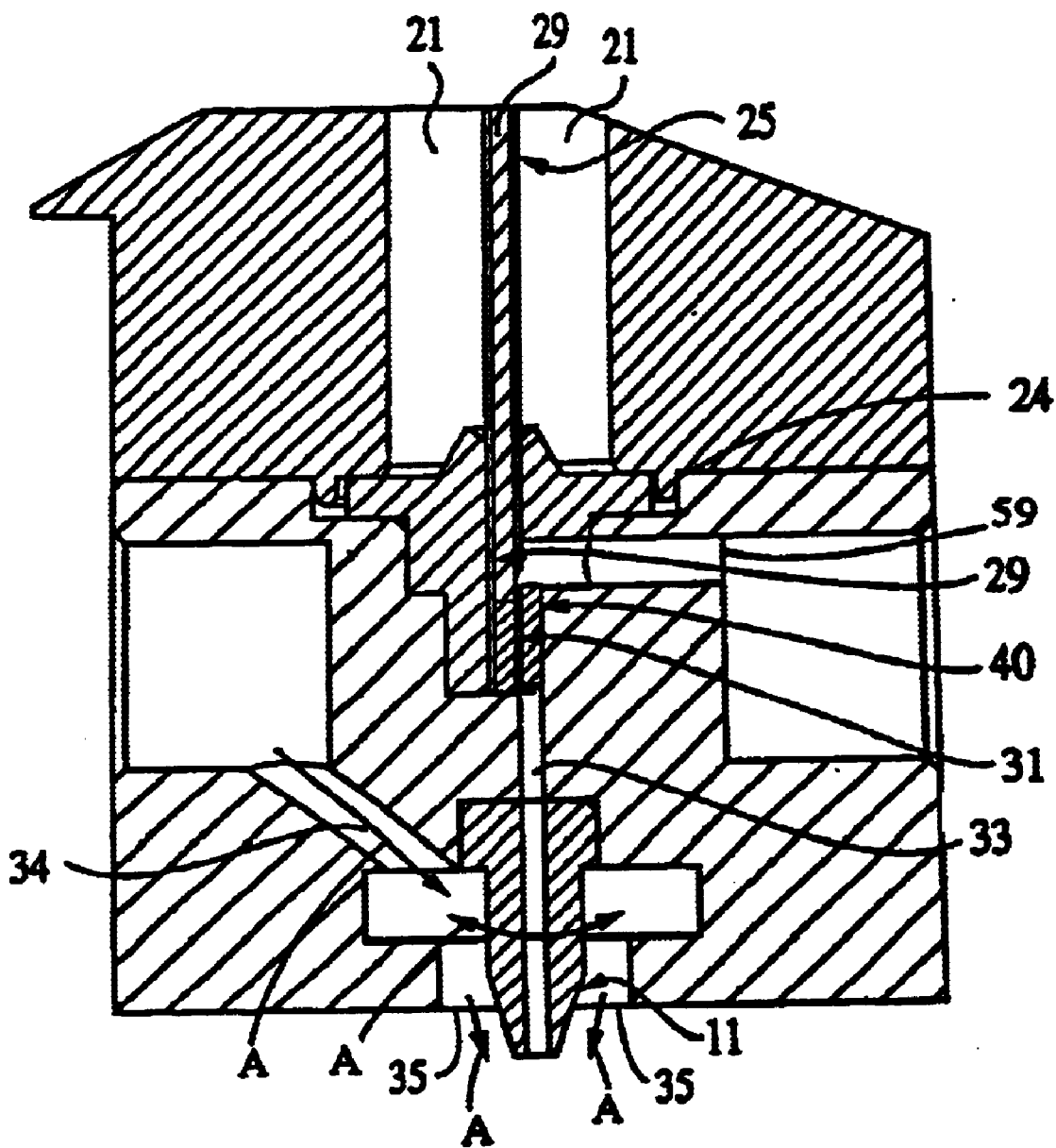
FIG. 11 is the same as FIG. 10, except that it shows a metered amount of liquid in an upper region of a fluid flow path, and arrows indicating flow of compressed gas through a compressed gas path.

FIG. 11 is the same as FIG. 10, except that it shows the expelled liquid 40, in an upper region of fluid output channel 33, and arrows A indicating flow of compressed air through a compressed gas path 34, and exit of the compressed air from an annular compressed gas outlet 35 surrounding nozzle tip 11. The exiting air forms an annular curtain of air moving downward and surrounding a droplet of liquid that will exit from nozzle tip 11. The annular curtain of air facilitates controlled movement of the droplet into the correct well, and effectively isolates all droplets and corresponding wells from each other.

Figure 12:
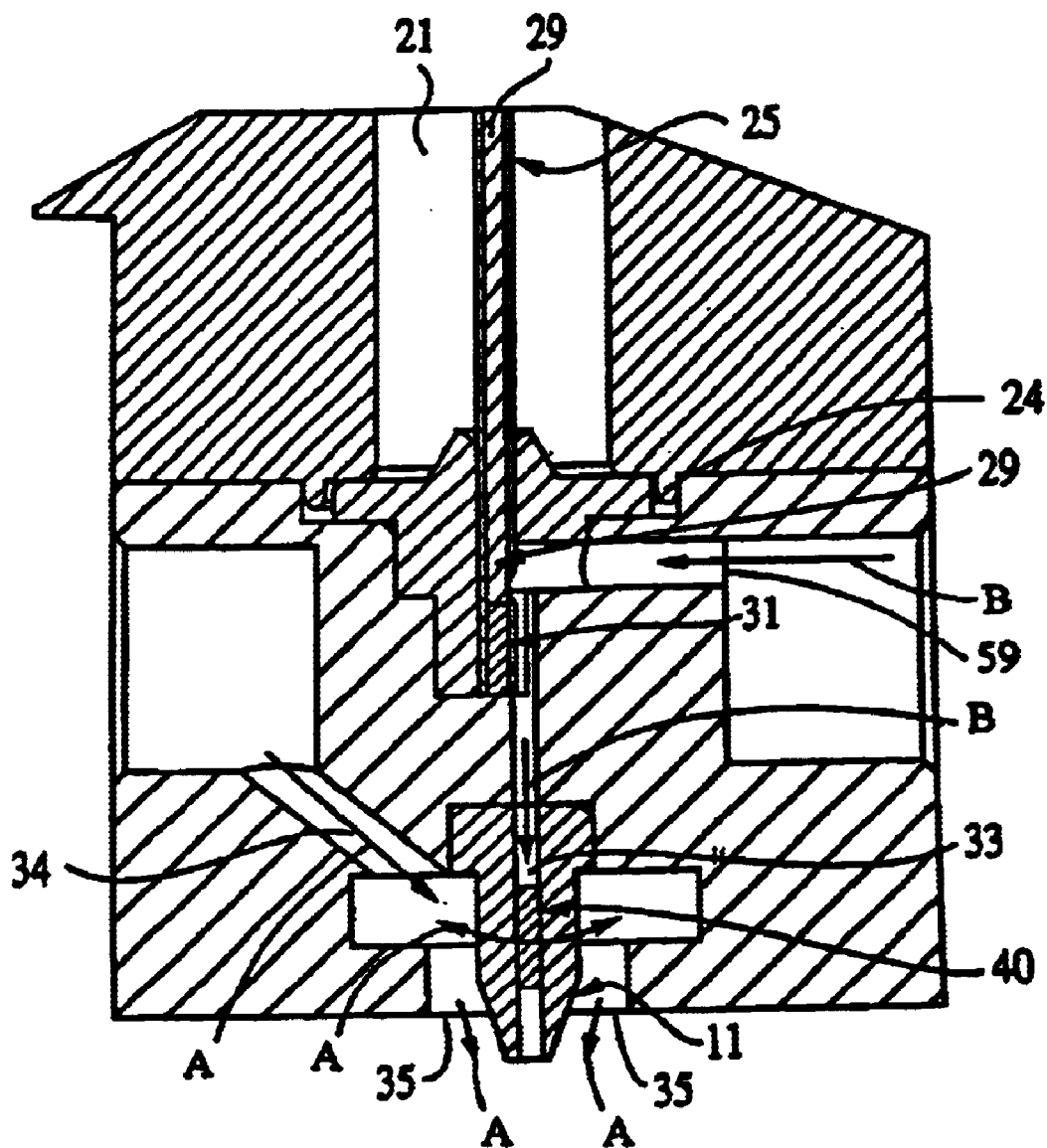
FIG. 12 is the same as FIG. 11, except that it shows the metered amount of liquid in a middle region of the fluid flow path, and arrows indicating flow of compressed gas sweeping the liquid down the fluid flow path.
Figure 13:
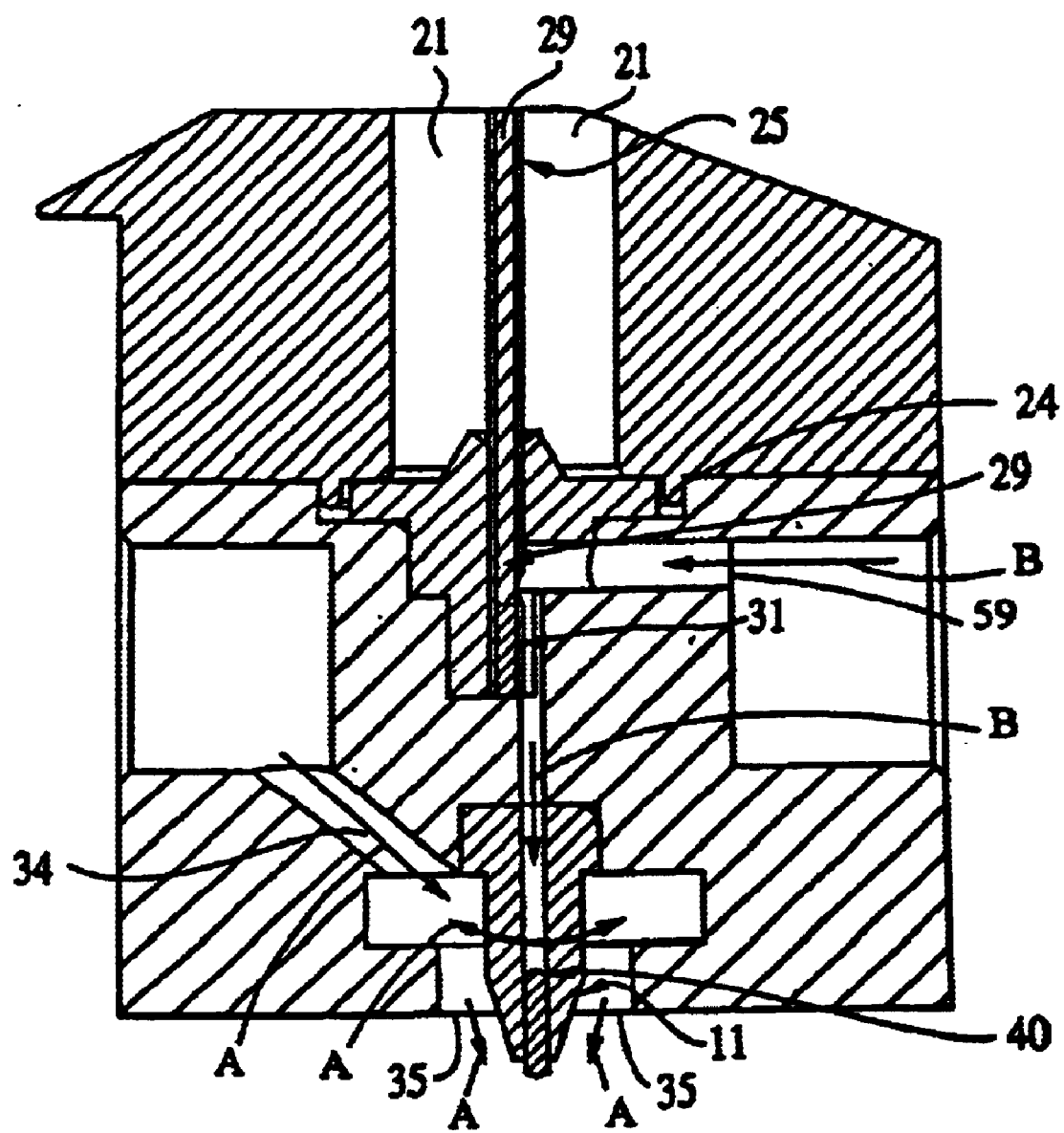
FIG. 13 is the same as FIG. 12, except that it shows the liquid in the lowermost portion of the fluid flow path, where the liquid is exiting from a flow path tip.

FIG. 12 is the same as FIG. 10, except that it shows a metered amount of expelled 4 liquid 40 (bolus), in a middle region of fluid output channel 33, and arrows B indicating flow of compressed air in fluid output channel 33. Air flowing from compressed gas inlet 59 through fluid output channel 33 sweeps liquid 40 down fluid output channel 33. FIG. 13 shows liquid 40 in the lowermost portion of fluid output channel 33, where it is exiting nozzle tip 11.

Figure 14:
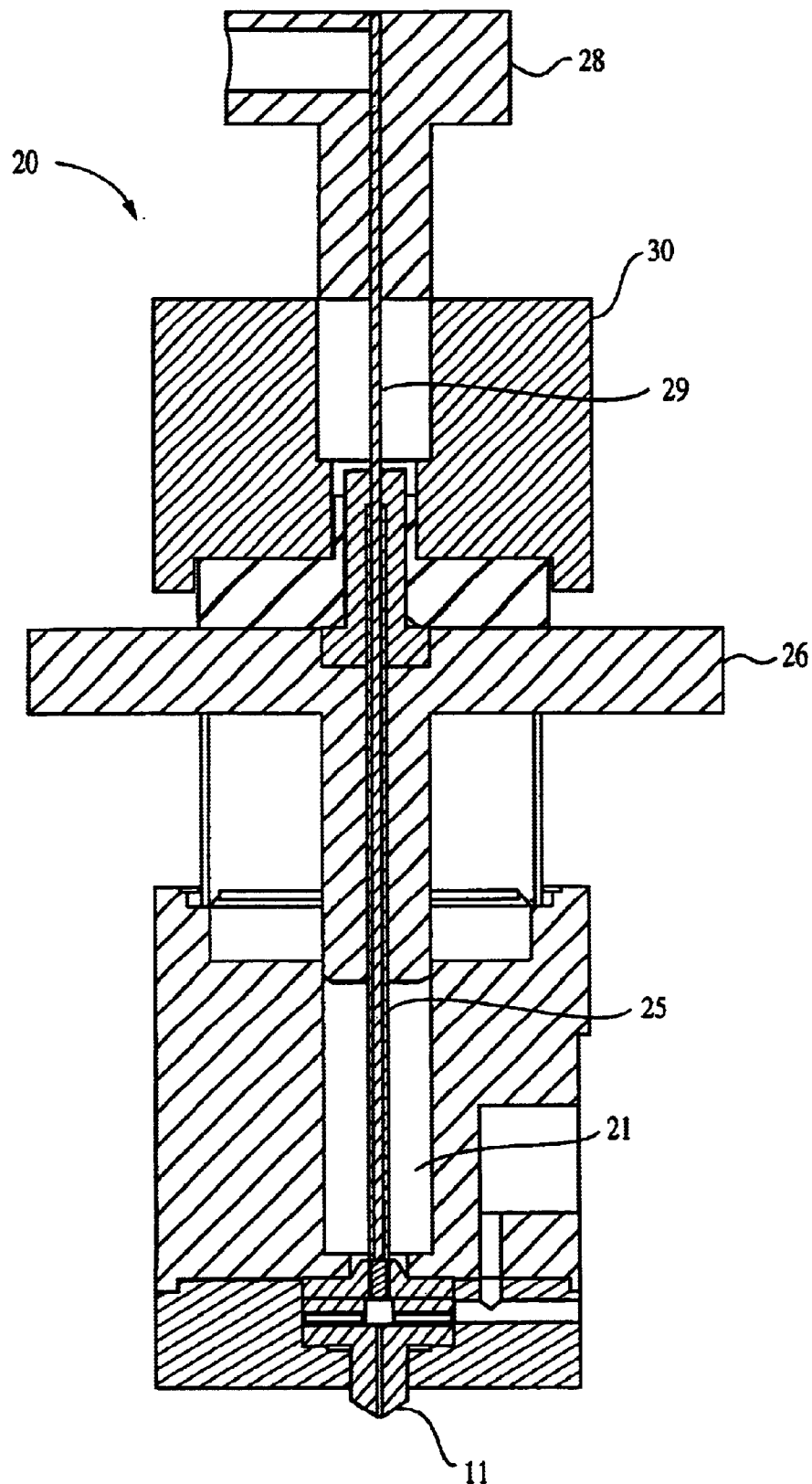
FIG. 14 is a sectional view of a single reservoir/tap unit. The unit has a metering tube in the up position.
Figure 15:
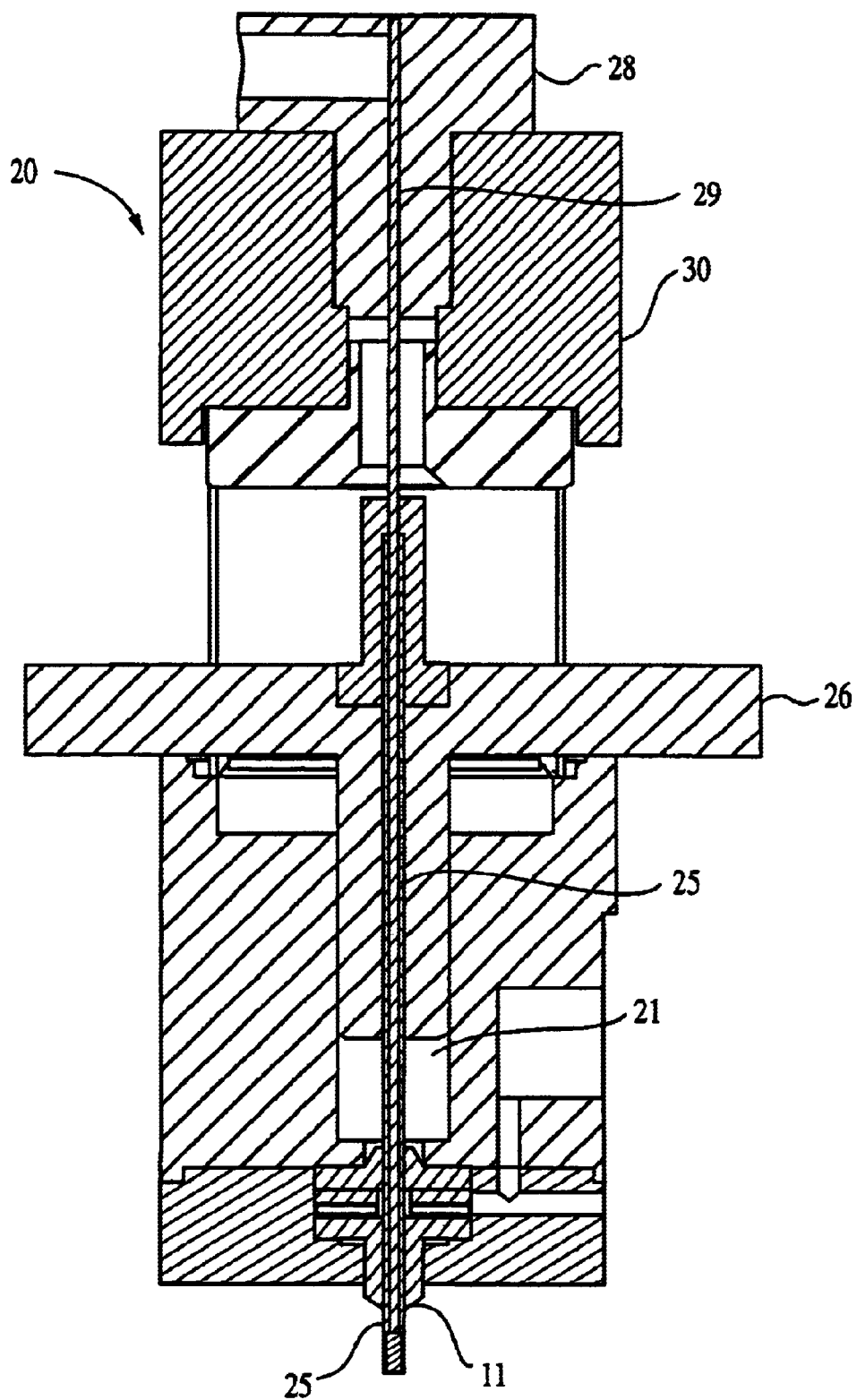
FIG. 15 is a sectional view of the reservoir/tap unit shown in FIG. 14, but with the metering tube in the down position.

FIG. 14 is a sectional view of a single reservoir/tap unit 20. The unit 20 contains a reservoir 21 formed by a cylinder wall 22 and lower seal 24. The unit 20 also contains a metering tube 25, tube handle 26, piston handle 28, piston 29, and piston handle stop 30. The embodiment depicted in FIG. 14 is an example of an in-line nozzle embodiment, because nozzle tip 11 is directly in line with metering tube 25. FIG. 14 shows the tube 25 and tube handle 26 in the up position. Tube handle 26 and piston handle 28 are included in each mechanical interface 16 shown in FIG. 1. FIG. 15 is a sectional view corresponding to FIG. 14, except that tube 25 is in the down position.

Figure 16:
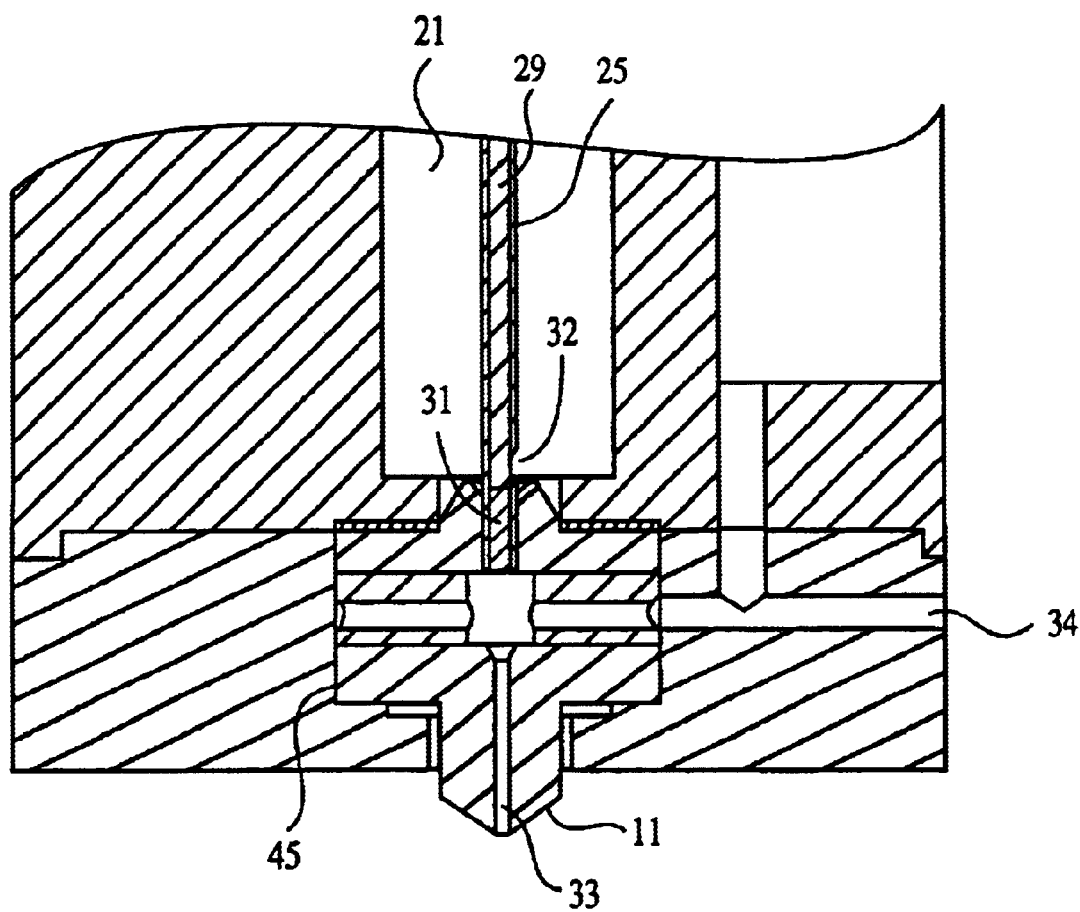
FIG. 16 is a detail from FIG. 14. The enlarged detail view shows the tube in the up position, and a piston in the tube. The piston is in the down position, where it rests against a tube plug.
Figure 17:
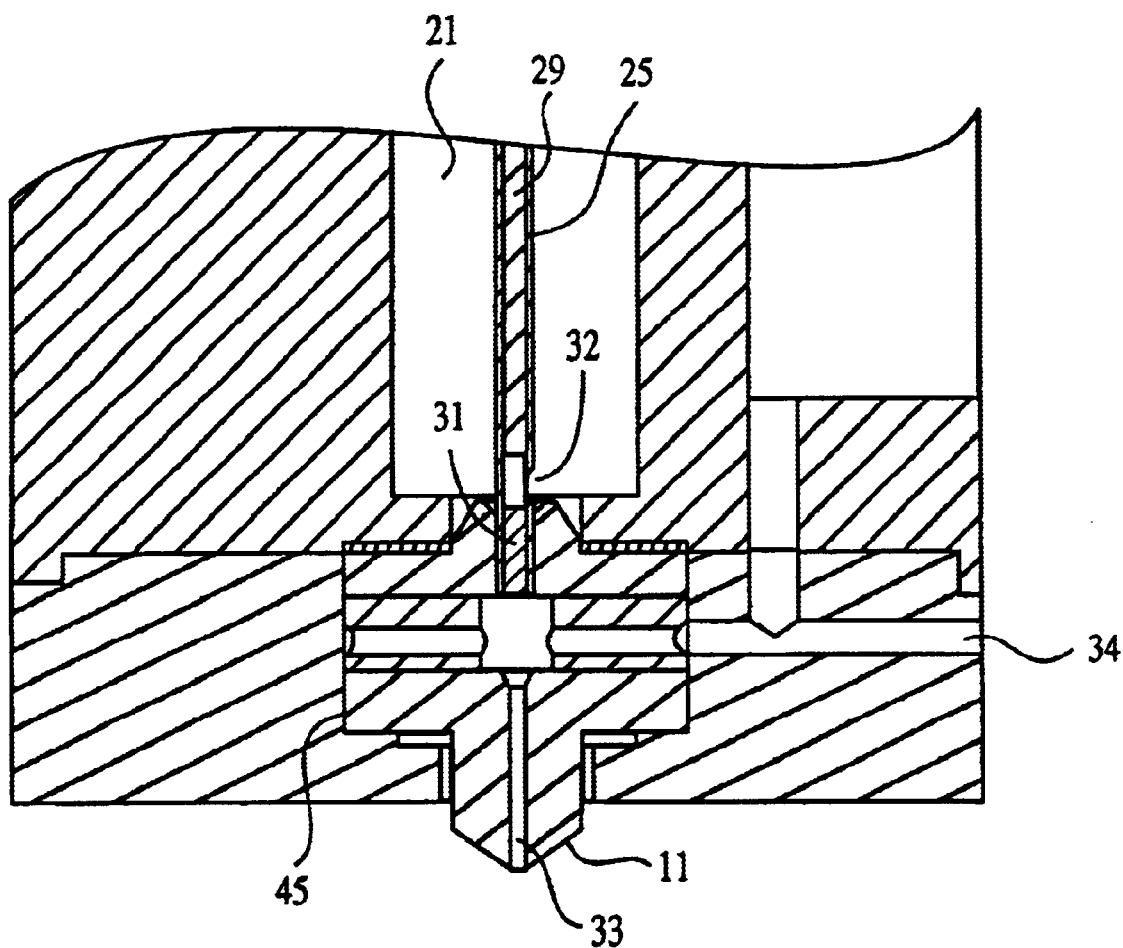
FIG. 17 is the same as FIG. 16, except that the piston is raised into an up position.

FIG. 16 is a detail from FIG. 14, in which tube 25 is in the up position and piston 29 is in the down position. In the down position, piston 29 rests against tube plug 31 so that piston 29 closes and seals tube port 32, thereby blocking entry of liquid from reservoir 21 into tube 25. FIG. 17 is the same as FIG. 16, except that piston 29 is raised into an up position. Raising piston 29 opens tube port 32 and draws a metered amount of liquid from reservoir 21 into tube 25, with the metered amount depending on the height to which piston 29 is raised.

Figure 18:
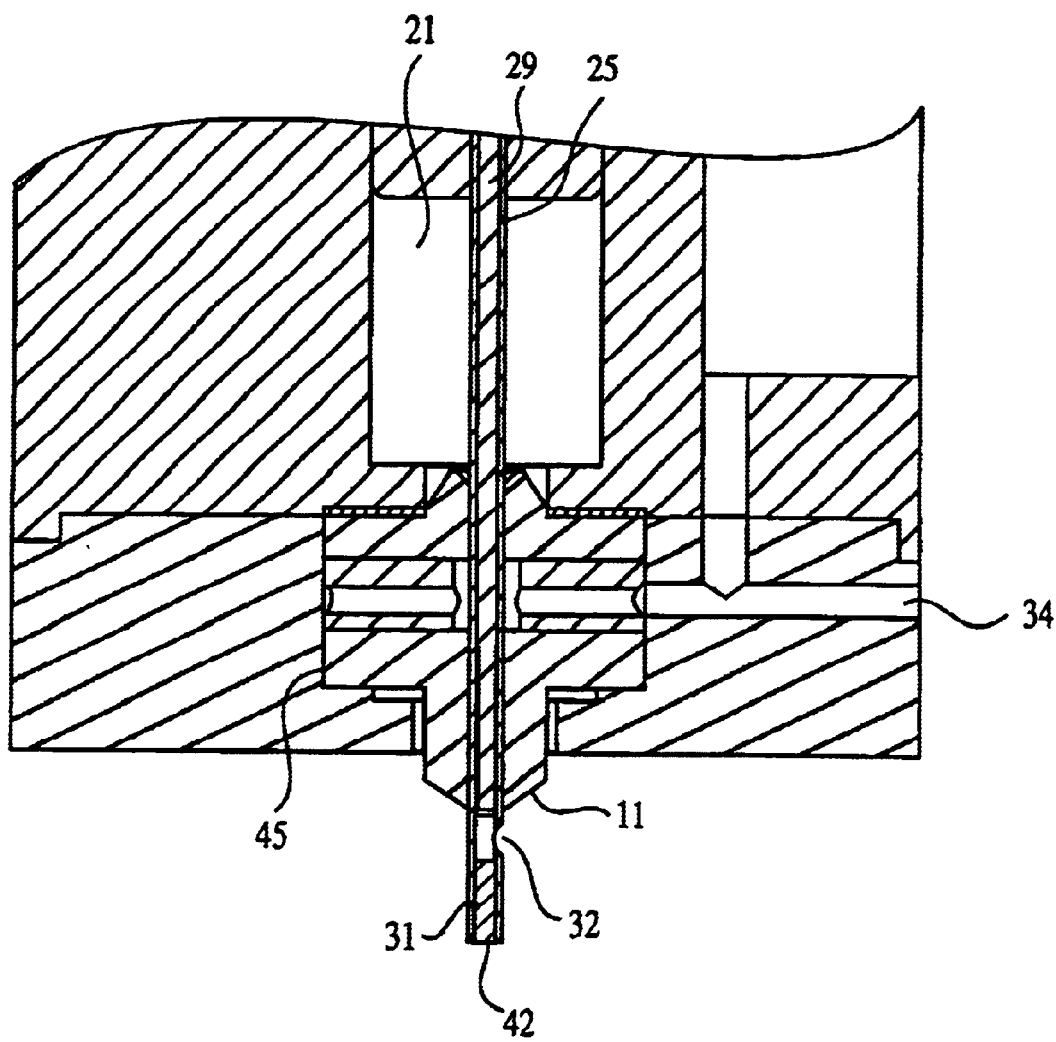
FIG. 18 is a sectional view (detail) of a reservoir/tap unit in which the metering tube is in the down position, and the piston is in an up position.
Figure 19:
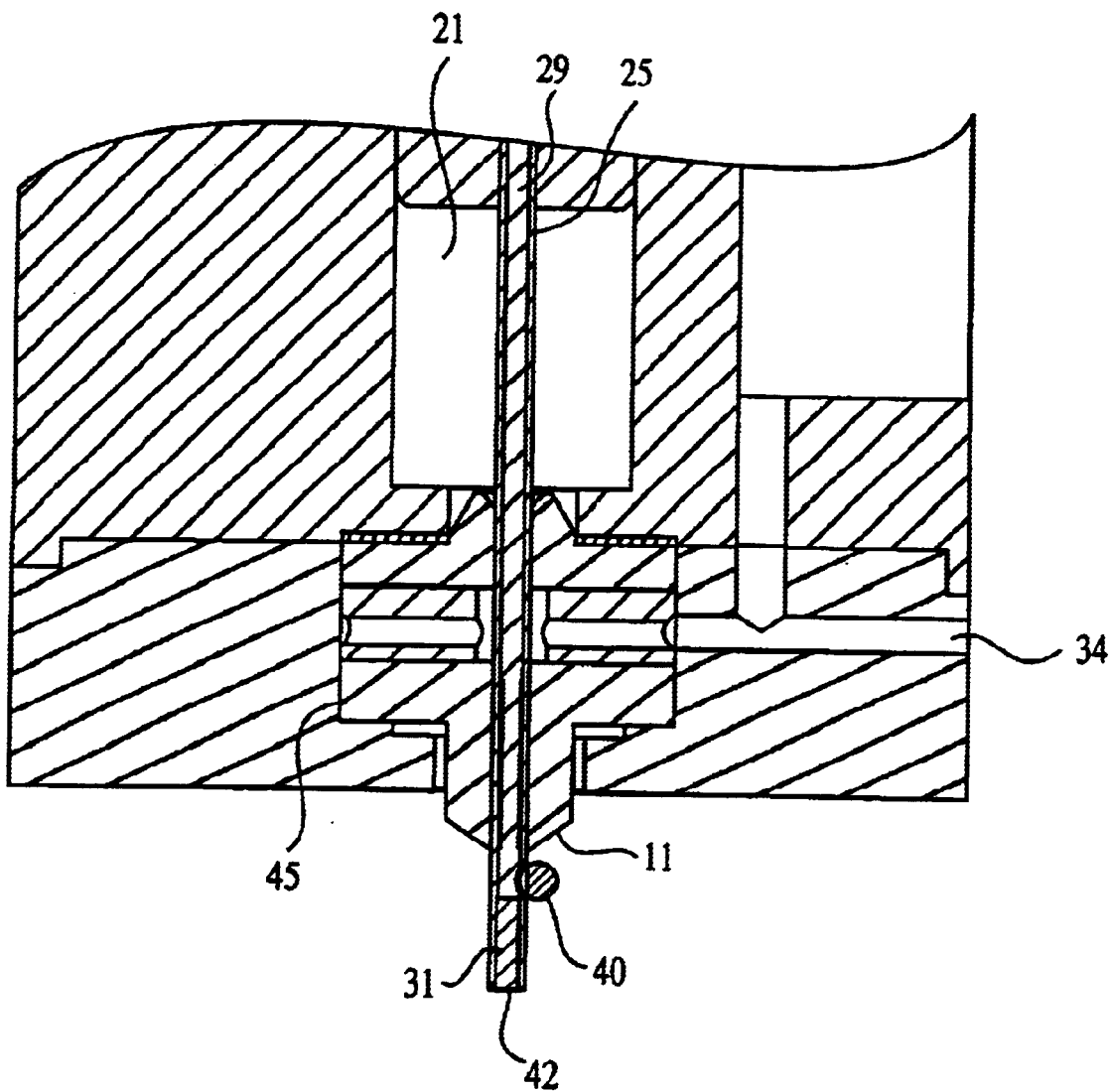
FIG. 19 is a sectional view (detail) of a reservoir/tap unit in which the metering tube is in the down position, and the piston is in the down position.

In FIG. 18, metering tube 25 has been translated downward into the down position, with piston 29 remaining in the up position, i.e., same position relative to tube 25. In this in-line nozzle embodiment of the invention, tube 25 passes through fluid output channel 33 as it translates between the up position and the down position. In the down position, port 32 is beneath nozzle tip 11. The next sequential step is lowering of piston 29 into the down position, in which piston 29 rests against tube plug 31, as shown in FIG. 19. This lowering of piston 29 expels liquid from tube 25 through port 32.

Figure 20:
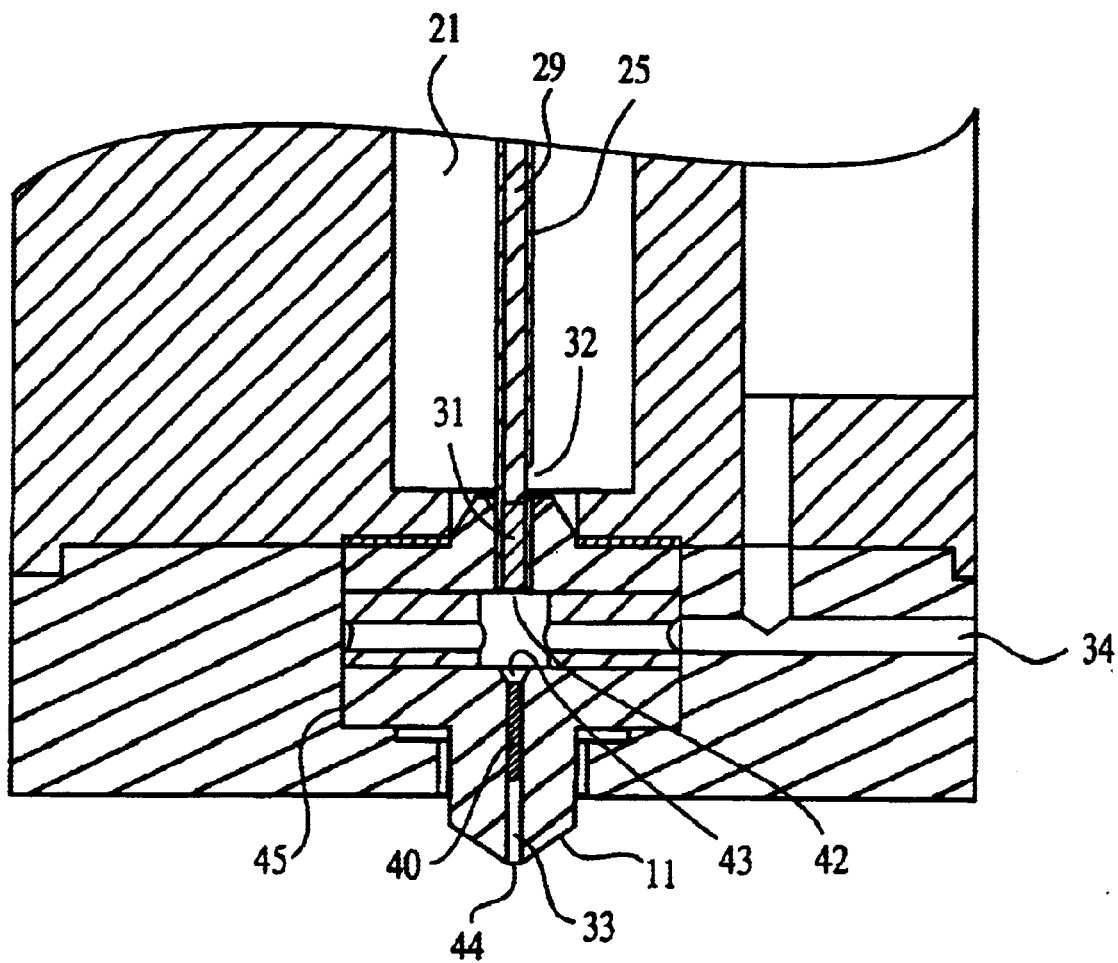
FIG. 20 is a sectional view (detail) of a reservoir/tap unit (in-line nozzle) in which the metering tube has been withdrawn from the down position to the up position, after expulsion of a bolus of liquid. The liquid has been drawn into the fluid output channel in the nozzle.

A bolus of expelled liquid 40 is shown in FIG. 19. Expelled liquid 40 clings to the side of tube 25 as a result of surface tension and adhesion. As tube 25 is retracted, nozzle tip 11 forces expelled liquid 40 to slide down the outside of tube 25. During retraction, when bottom end 42 of tube 25 reaches lower end 44 of fluid output channel 33, expelled liquid 40 migrates to bottom end 42 of tube 25 and clings there. As tube 25 is further retracted, expelled liquid 40 follows bottom end 42 of tube 25 upward through fluid output channel 33 (FIG. 20). When bottom end 42 of tube 25 reaches upper end 43 of fluid output channel 33, expelled liquid 40 detaches from bottom end 42 of tube 25 and remains in upper portion of fluid output channel 33. When tube 25 is fully retracted into up position, compressed air enters compressed gas path 34 and pushes expelled liquid 40 downward, so that it exits nozzle tip 11 and falls into a well in a microtiter plate (not shown).

In in-line nozzle embodiments of the invention, nozzle 45 preferably is made of an elastomeric material, with fluid output channel 33 having an inside diameter slightly smaller than the outside diameter of tube 25. Fluid output channel 33 expands slightly to accommodate tube 25, as the tube passes through the fluid output channel. This promotes an airtight seal between tube 25 and fluid output channel 33, when the tube is in the channel. Selection of a suitable elastomer is within ordinary skill in the art.

Figure 21:
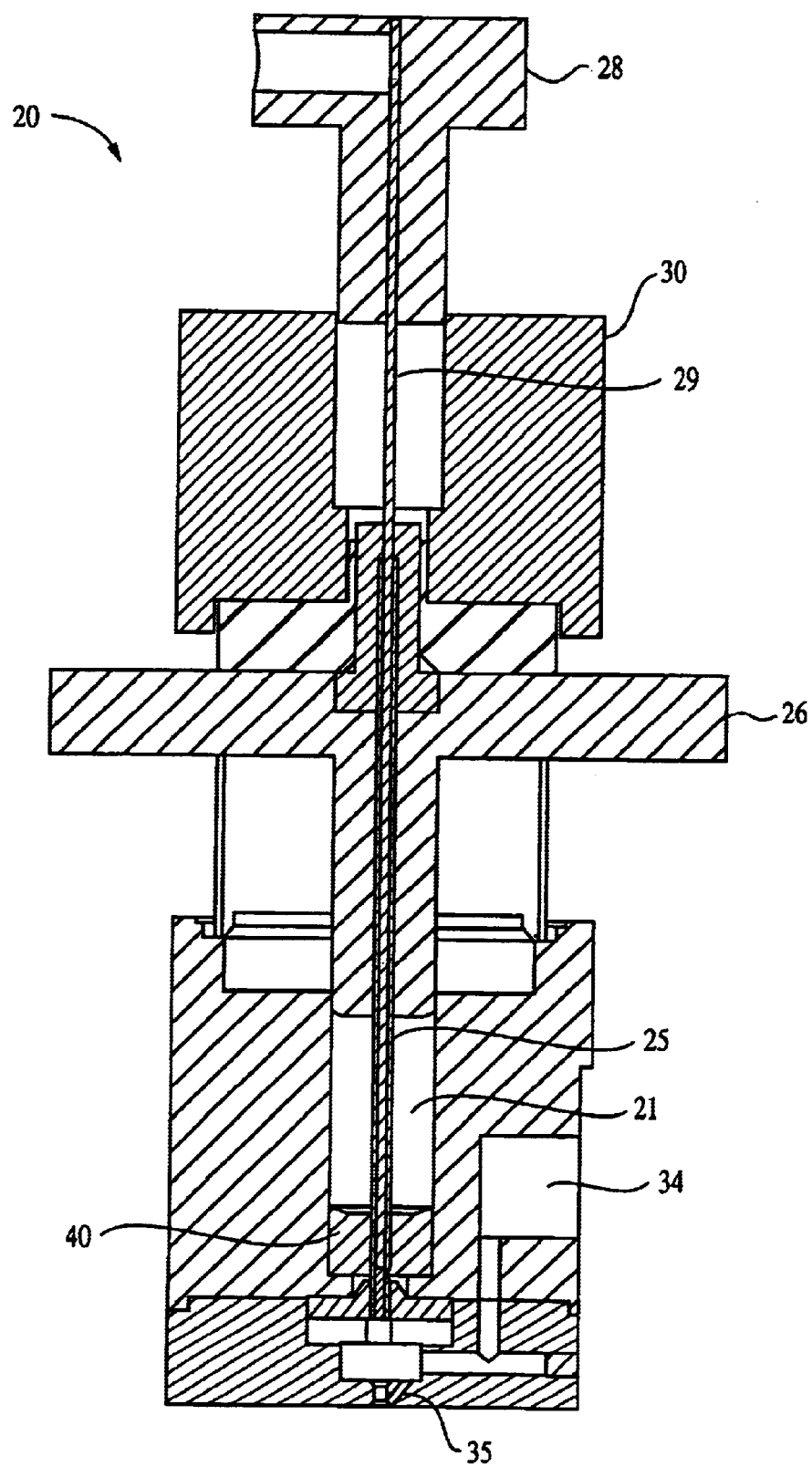
FIG. 21 is a sectional view of a single nozzleless tapped reservoir unit with the metering tube in the up position.
Figure 22:
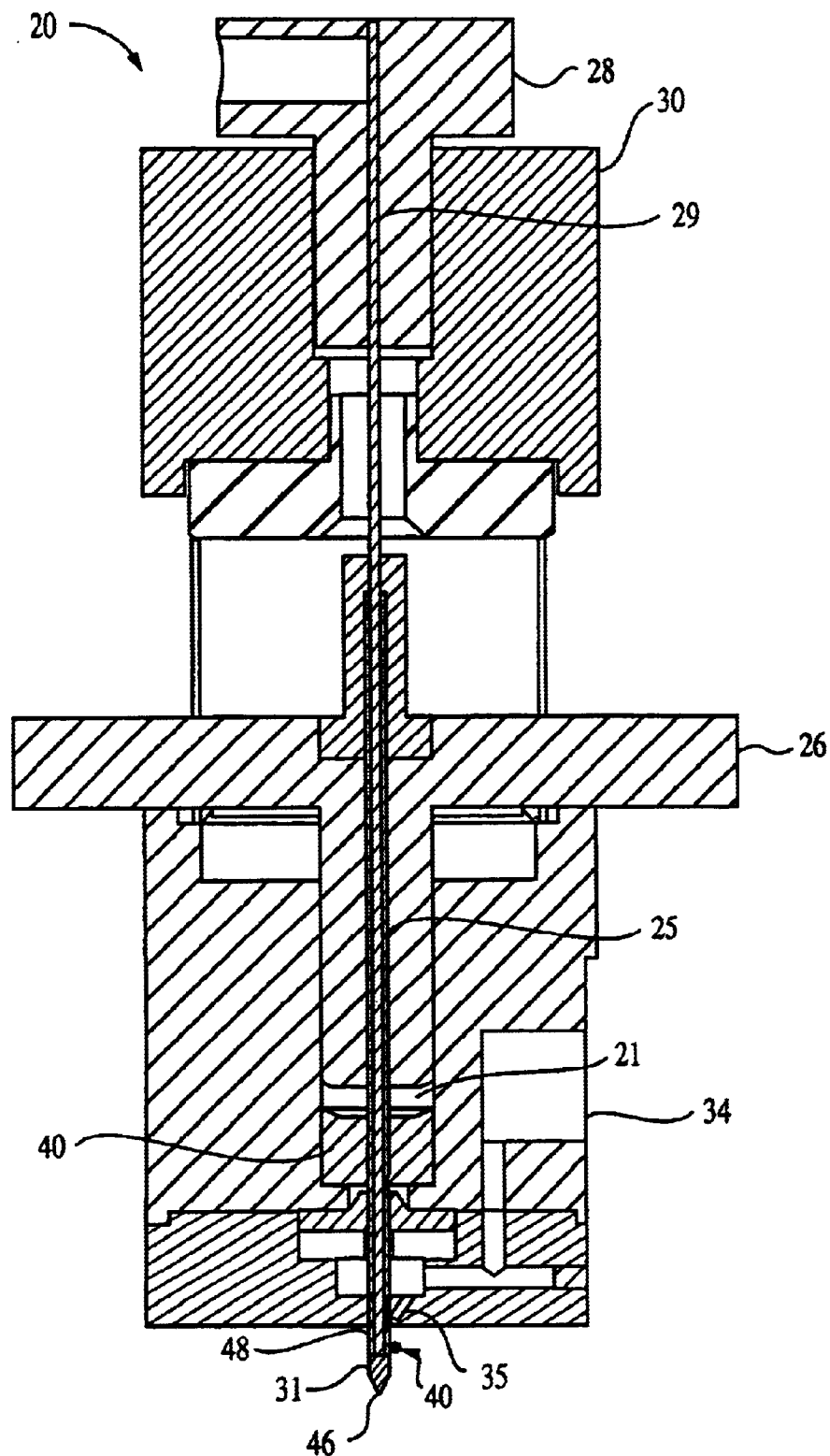
FIG. 22 is a sectional view of a nozzleless reservoir/tap unit with the metering tube in the down position. A bolus of expelled liquid is shown at the port.
Figure 23:
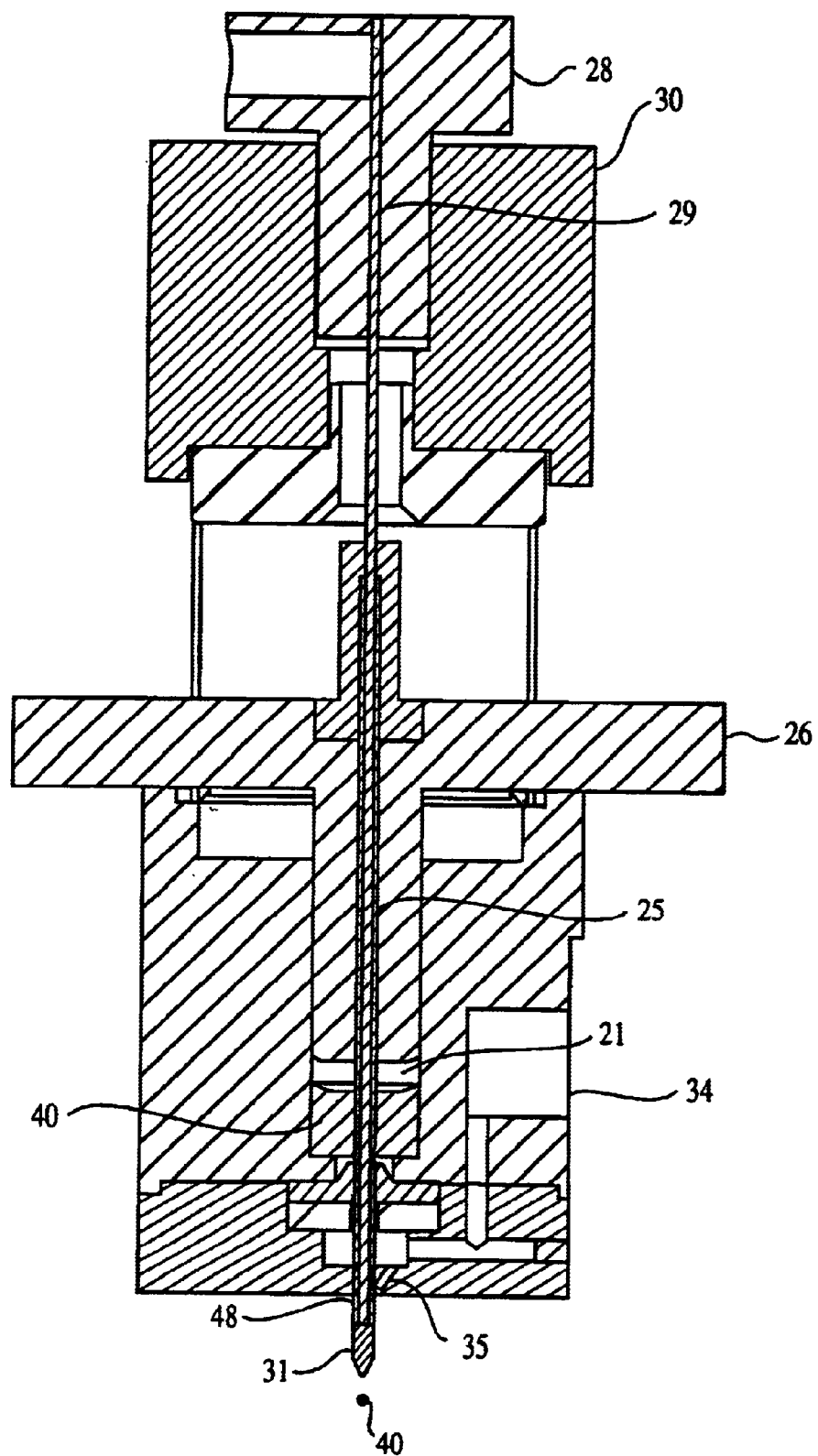
FIG. 23 is a sectional view of a nozzleless reservoir/tap unit with the metering tube in the down position. A bolus of expelled liquid is shown in flight after being propelled from the tip of the metering tube.
Figure 24:
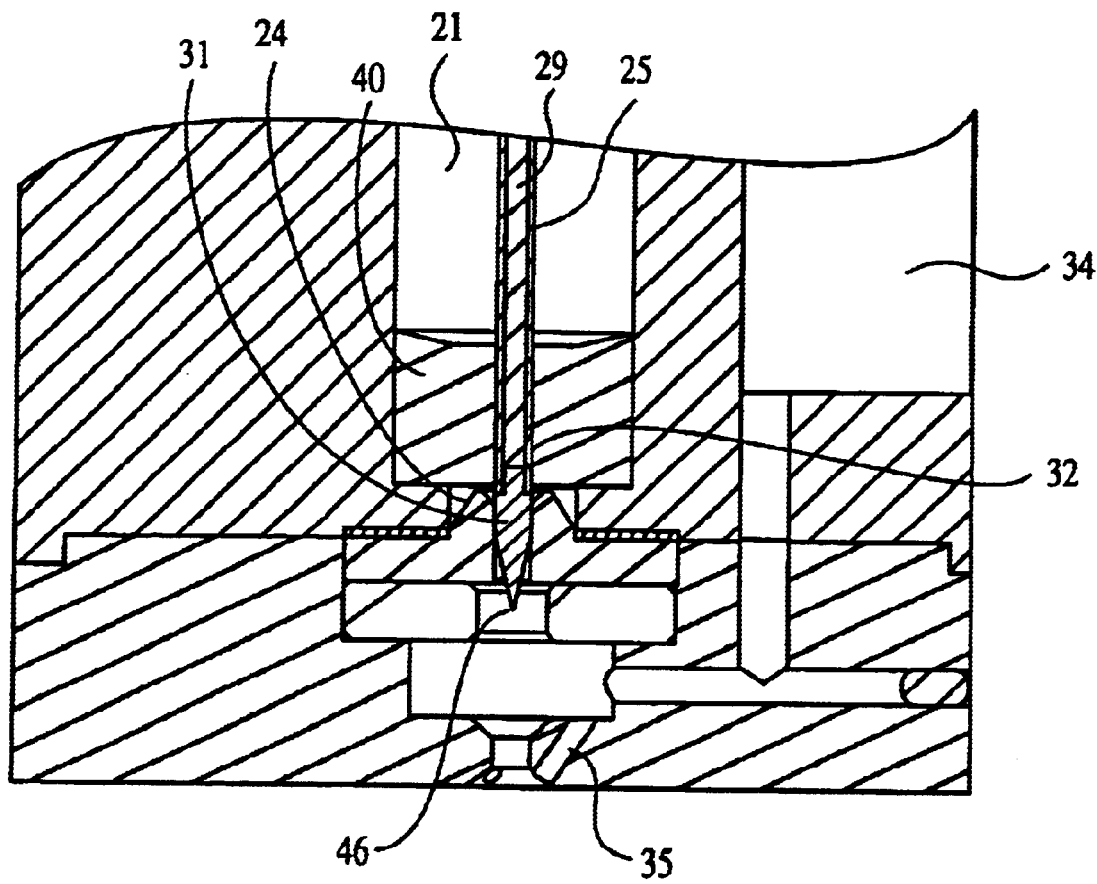
FIG. 24 is a detail from FIG. 21. The enlarged detail view shows the metering tube in the up position and the piston in the down position.
Figure 25:
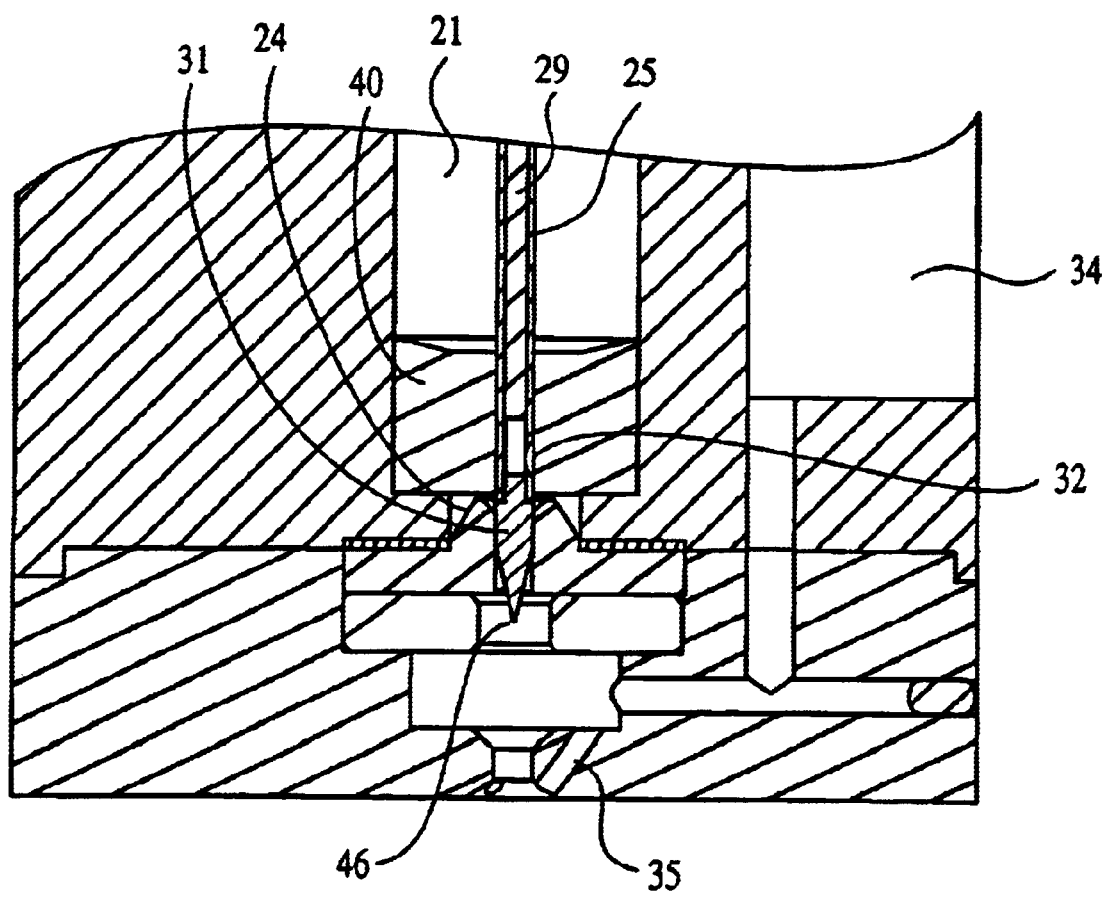
FIG. 25 is the same as FIG. 24, except that the metering tube is in the up position and the piston is in the up position.
Figure 26:
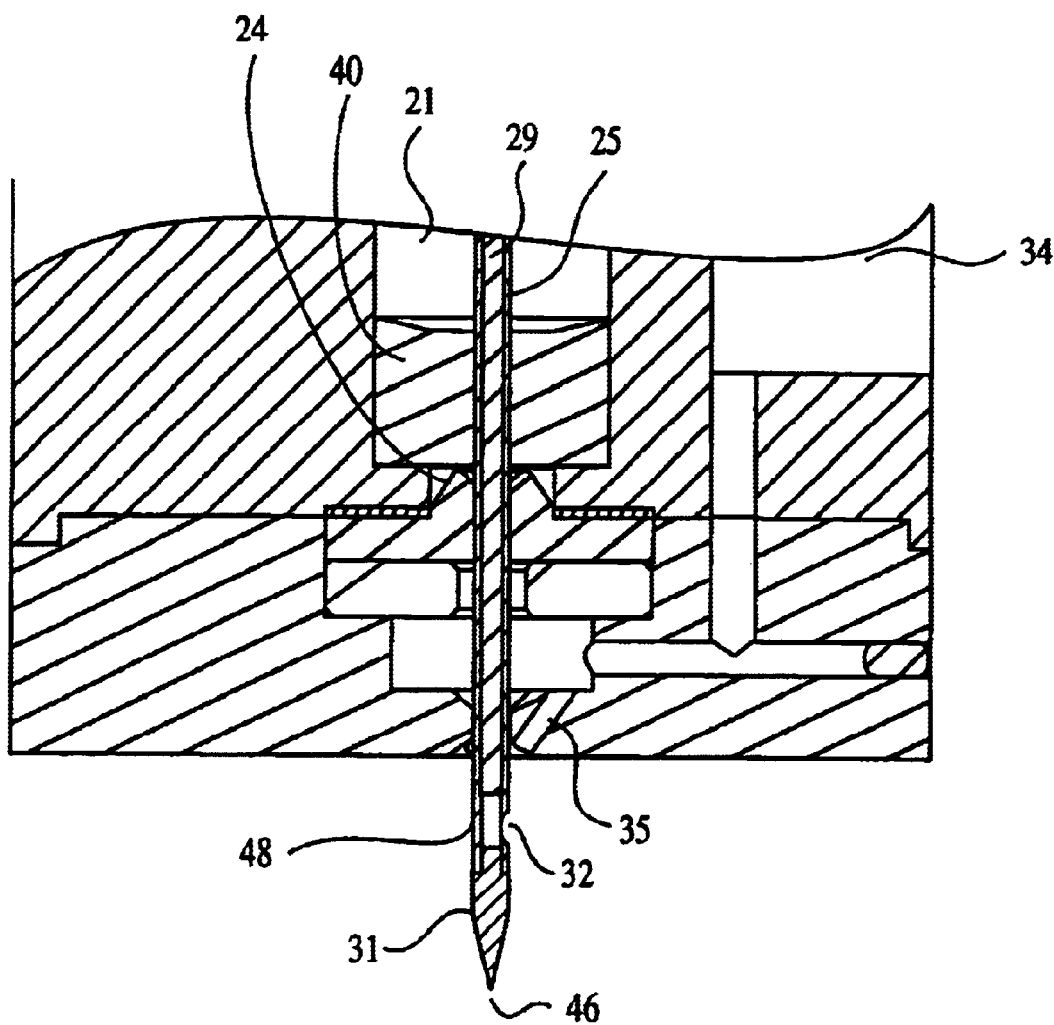
FIG. 26 is the same as FIG. 24, except that the metering tube is in the down position and the piston is in the up position.
Figure 27:
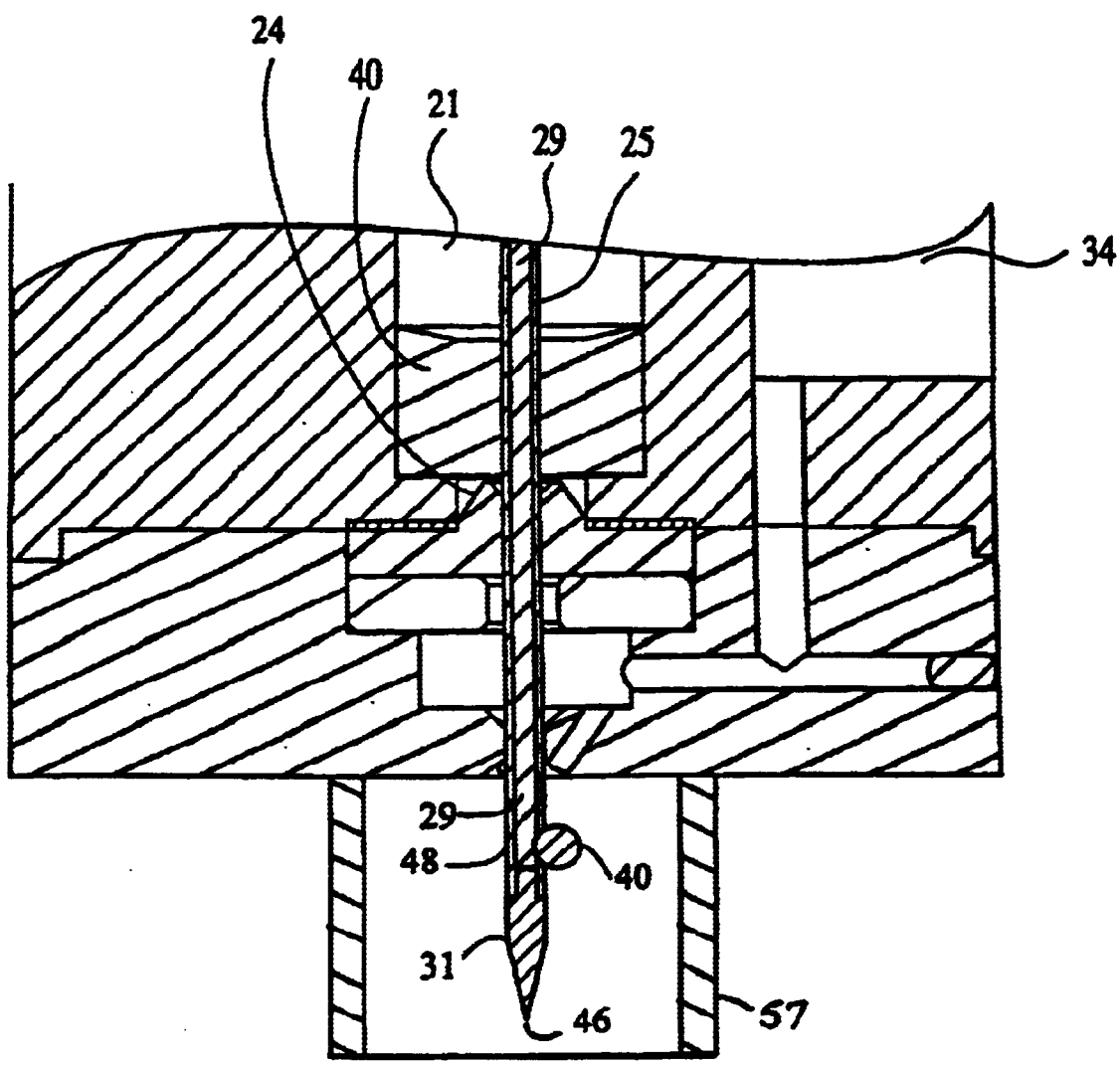
FIG. 27 is the same as FIG. 24, except that the metering tube is in the down position and the piston is in the down position.

FIGS. 21–27 depict a nozzleless tapped reservoir. In FIG. 21 reservoir/tap unit 20 has metering tube 25 in the up position and piston 29 in the down position. FIG. 24 is a detail from FIG. 21 in which tube 25 is in the up position and piston 29 is in the down position. In the down position, piston 29 rests against tube plug (tube end closure) 31 so that piston 29 closes and seals tube port 32, thereby blocking entry of liquid 40 from reservoir 21. FIG. 25 is the same as FIG. 24, except that piston 29 is raised into an up position. Raising piston 29 opens tube port 32 and draws a metered amount of liquid from reservoir 21 into tube 25, with the metered amount depending on the height to which piston 29 is raised. In FIG. 26, metering tube 25 has been translated downward into the down position, with piston 29 remaining in the up position. In this nozzleless embodiment of the invention, no fluid output channel or nozzle is necessary, and port 32 and fine point 46 are exposed (FIG. 22). The next sequential step is lowering of piston 29 into the down position, where it rests against tube plug 31, (FIG. 27). This expels a precisely metered amount of liquid 40 through port 32. Expelled liquid 40 is then swept downward by a downward flow of air from compressed gas outlet 35. FIG. 23 shows expelled liquid 40 dropping from bottom end 42 of metering tube 25, which is tapered to a fine point 46. Fine point 46 facilitates release of expelled liquid 40 from bottom end 42 of metering tube 25 in a controlled manner. In some embodiments of the invention, a shroud 57 surrounds or partially shields the lower end 48 of metering tube 25, which extends downward when metering tube 25 is in the expel position.

Figure 28C:
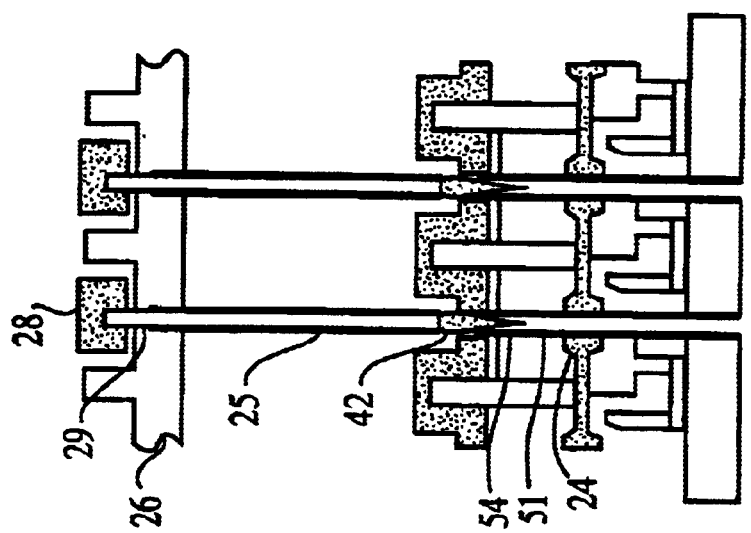
FIGS. 28A–28F are sectional views depicting a device and sequence of events in a preferred packaging method.
Figure 28B:
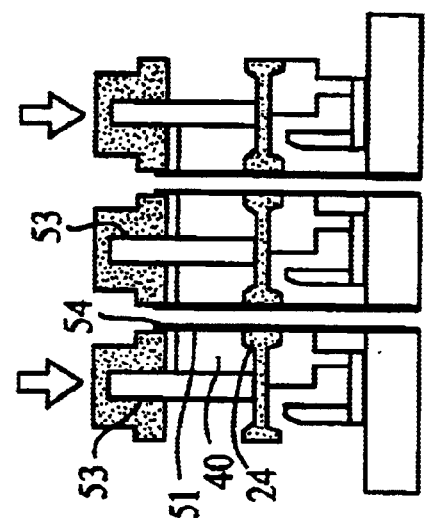
Figure 28A:
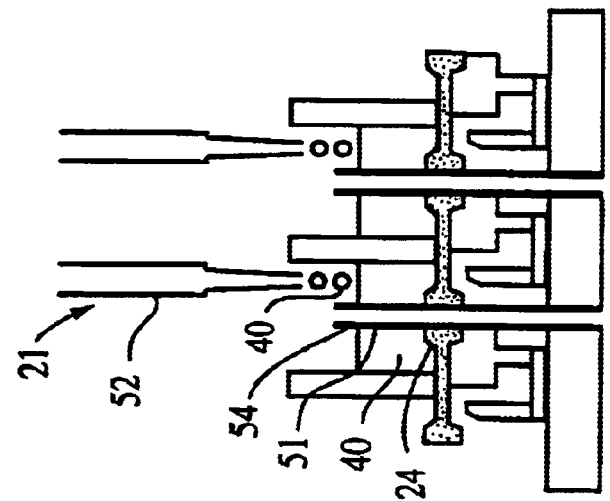
Figure 28F:
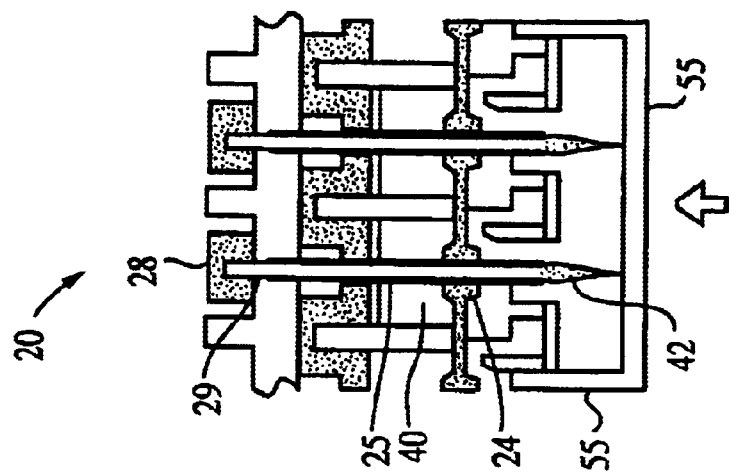
Figure 28E:
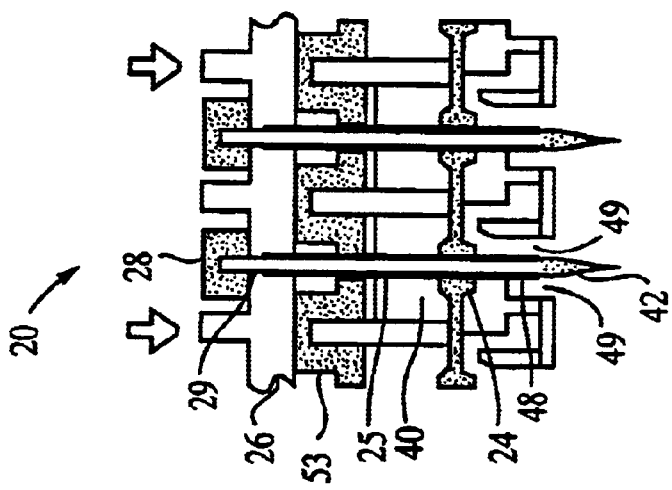
Figure 28D:
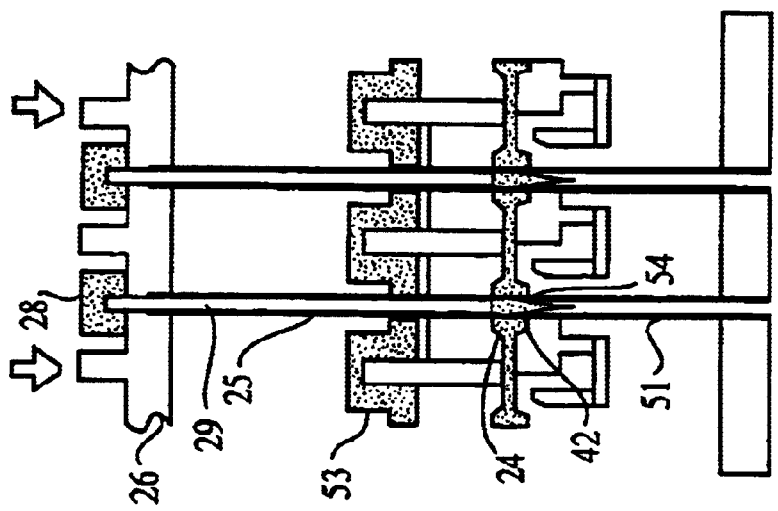

FIGS. 28A–28F depict a device and sequence of events in a preferred packaging method according to the invention. Two reservoir/tap units in an array are depicted. In FIG. 28A fill pin 51, which has an outside diameter equal to that of metering tube 25, extends upward through lower seal 24. This permits dispensing of liquid 40 into reservoir 21 from reservoir filling device 52 positioned above the reservoir. In FIG. 28B cap seal 53 is installed on top of reservoir 21. In FIG. 28C metering tube 25 is aligned directly above fill pin 51, so that tube bottom end 42 contacts upper end 54 of fill pin 51. In FIG. 28D metering tube 25 is lowered so as to push fill pin 51 downward. By this process, metering tube 25 replaces fill pin 51 without allowing leakage of liquid 40 from reservoir 21. In FIG. 28E metering tube 25 is seated against lower seal 24. In FIG. 28F protective cover 55 is installed on bottom of device 20 for storage. In FIG. 28E it can be seen that the lower portion of the device serves as a shroud 49 around the lower end 48 of metering tube 25.

Devices according to the invention can be designed for compatibility with various liquids, including aqueous buffers, organic solvents, e.g., dimethylsulfoxide, acids and bases. Compatibility is achieved by selection of suitable materials for fabrication of components that contact the liquid. Exemplary materials for fabrication of components are stainless steel, nylon, polyethylene, polypropylene, EPD rubber and polytetrafluoroethylene (PTFE; Teflon®). Selection of suitable materials and fabrication of components is within ordinary skill in the art.

It is to be understood that various modifications on the above-described embodiments can be made without departing from the spirit and scope of the invention. For example, to form a liquid reservoir, sliding seal 23 and lower seal 24 can be replaced with an expandable bladder. Accordingly, other embodiments of the invention are within the scope of the following claims.

What is claimed is:

1. A device for storing a liquid and dispensing metered, nanoliter or microliter amounts of the liquid into a liquid-receiving unit, the device comprising:

a sealed, tapped reservoir comprising an integrated metering tap, the tap comprising:

(a) a metering tube translatable between a fill position inside the reservoir and an expel position outside the reservoir, the metering tube comprising (1) a tube end closure in a lower portion of the tube, (2) a port above the tube end closure, and (3) a piston in an upper portion of the tube, the piston being movable within the tube between a down position that seals the port and an up position above the port, and (b) a fluid output channel having an upper portion in fluid communication with the port when the tube is in the expel position and a lower portion terminating in a nozzle tip.

2. The device of claim 1, wherein a full stroke movement of the piston from an uppermost position to a lowermost position displaces from 10 nanoliters to 20 microliters of volume.

3. The device of claim 2, wherein the full stroke movement of the piston displaces from 20 nanoliters to 2 microliters of volume.

4. The device of claim 3, wherein the full stroke movement of the piston displaces from 50 nanoliters to 500 nanoliters of volume.

5. The device of claim 1, further comprising a compressed gas inlet in fluid communication with the fluid output channel at a point upstream of the port when the tube is in the expel position.

6. The device of claim 5, further comprising a compressed gas path terminating in an annular opening surrounding the fluid output tip.

7. A device for storing a liquid and dispensing metered, nanoliter or microliter amounts of the liquid into a liquid-receiving unit, the device comprising:

a sealed reservoir comprising an integrated metering tap, the tap comprising:

(a) a metering tube translatable between a fill position inside the reservoir and an expel position outside the reservoir, the metering tube comprising (1) a tube end closure in a lower portion of the tube, (2) a port above the tube end closure, and (3) a piston in an upper portion of the tube, the piston being movable within the tube between a down position that seals the port and an up position above the port; and (b) a nozzle comprising a fluid output channel through which the tube including the tube end closure and the port, extends when in the expel position, the fluid output channel having an upper end in fluid communication with a compressed gas path, and a lower end terminating in a nozzle tip.

8. The device of claim 7, wherein a full stroke movement of the piston from an uppermost position to a lowermost position displaces from 10 nanoliters to 20 microliters of volume.

9. The device of claim 8, wherein the full stroke movement of the piston displaces from 20 nanoliters to 2 microliters of volume.

10. The device of claim 9, wherein the full stroke movement of the piston displaces from 50 nanoliters to 500 nanoliters of volume.

11. A device for storing a liquid and dispensing metered, nanoliter or microliter amounts of the liquid into a liquid-receiving unit, the device comprising:

a sealed, tapped reservoir comprising an integrated metering tap, each tap comprising:

(a) a metering tube translatable between a fill position inside the reservoir and an expel position outside the reservoir, the metering tube comprising
  (1) a tube end closure in a lower portion of the tube,
  (2) a port above the tube end closure,
  (3) a piston in an upper portion of the tube, the piston being movable within the tube between a down position that seals the port and an up position above the port, and
  (4) a lower end;

(b) a compressed gas path comprising a compressed gas outlet located above the port to deliver a downward gas stream across the port when the metering tube is in the expel position; and (c) a fluid output channel through which the tube, including the tube end closure and the port, in the expel position, the fluid output channel having an upper end in fluid communication with a compressed gas path, and a lower end open to the liquid receiving unit.

12. The device of claim 11, wherein a full stroke movement of the piston from an uppermost position to a lowermost position displaces from 10 nanoliters to 20 microliters of volume.

13. The device of claim 12, wherein the full stroke movement of the piston displaces from 20 nanoliters to 2 microliters of volume.

14. The device of claim 13, wherein the full stroke movement of the piston displaces from 50 nanoliters to 500 nanoliters of volume.

15. The device of claim 11, wherein the lower end of the metering tube is tapered to a point.

16. The device of claim 11, further comprising a shroud surrounding or partially shielding the lower end of the metering tube when the metering tube is in the expel position.

* * * * *